(12) United States Patent
Yang et al.

(10) Patent No.: US 12,115,233 B2
(45) Date of Patent: *Oct. 15, 2024

(54) IMAGING AND RADIOTHERAPEUTICS AGENTS TARGETING FIBROBLAST-ACTIVATION PROTEIN-α (FAP-α)

(71) Applicant: The Johns Hopkins University, Baltimore, MD (US)

(72) Inventors: Xing Yang, Baltimore, MD (US); Sridhar Nimmagadda, Baltimore, MD (US); Steven Rowe, Parkville, MA (US); Stephanie Slania, Baltimore, MD (US); Martin G. Pomper, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/585,905

(22) Filed: Feb. 23, 2024

(65) Prior Publication Data

US 2024/0293584 A1 Sep. 5, 2024

Related U.S. Application Data

(63) Continuation of application No. 18/354,282, filed on Jul. 18, 2023, now Pat. No. 11,938,201, which is a continuation of application No. 16/758,182, filed as application No. PCT/US2018/057086 on Oct. 23, 2018.

(60) Provisional application No. 62/575,607, filed on Oct. 23, 2017.

(51) Int. Cl.
A61K 51/00 (2006.01)
A61K 47/54 (2017.01)
A61K 51/04 (2006.01)
A61M 36/14 (2006.01)

(52) U.S. Cl.
CPC ........ A61K 51/0485 (2013.01); A61K 47/545 (2017.08); A61K 51/0478 (2013.01); A61K 51/0482 (2013.01)

(58) Field of Classification Search
CPC .............. A61K 51/0485; A61K 47/545; A61K 51/0478; A61K 51/0482
See application file for complete search history.

(56) References Cited

U.S. PATENT DOCUMENTS 9,346,814 B2    5/2016   Jansen et al.
2008/0280856 A1 11/2008  Cohen et al.
2010/0098633 A1  4/2010  Zimmerman et al.
2014/0357650 A1 12/2014  Jansen et al.
2020/0237936 A1  7/2020  Low et al.
2021/0038749 A1  2/2021  Haberkorn et al.

FOREIGN PATENT DOCUMENTS

EP    18199641.4         10/2018
JP    2021/512949 A       5/2021
WO    WO 2010/014933      2/2010
WO    WO 2010/108125      9/2010
WO    WO 2013/107820      7/2013
WO    WO 2014 /001538     1/2014
WO    WO 2015/114166      8/2015
WO    WO 2016/065142      4/2016
WO    WO 2016/149188      9/2016
WO    WO 2016/196628 A1  12/2016
WO    WO 2019/154886      8/2019

OTHER PUBLICATIONS

Allinen et al., Molecular characterization of the tumor microenvironment in breast cancer. Cancer Cell. Jul. 2004;6(1):17-32.
Azhdarinia et al., "Characterization of chemical, radiochemical and optical properties of a dual-labeled MMP-9 targeting peptide". Bioorganic & Medicinal Chemistry, vol. 19, Issue 12, May 6, 2011, 3769-3776.
Bae et al., Fibroblast activation protein alpha identifies mesenchymal stromal cells from human bone marrow. Br J Haematol. Sep. 2008;142(5):827-30.
Beebe et al., "Understanding the Apothecaries Within: The Necessity of a Systematic Approach for Defining the Chemical Output of the Human Microbiome". Clin Transl Sci. Feb. 2014; 7(1): 74-81.
Bernhard et al., DOTAGA-anhydride: a valuable building block for the preparation of DOTA-like chelating agents. Chemistry. Jun. 18, 2012;18(25):7834-41.
Chen et al., Advance of molecular imaging technology and targeted imaging agent in imaging and therapy. Biomed Res Int. 2014; 2014 : 819324. PMCID: PMC3943245.
Cho et al., Biodistribution, tumor detection, and radiation dosimetry of 18F-DCFBC, a low-molecular-weight inhibitor of prostate-specific membrane antigen, in patients with metastatic prostate cancer. Journal of nuclear medicine : official publication, Society of Nuclear Medicine. 2012; 53:1883-1891.
Coenen et al., Fluorine-18 radiopharmaceuticals beyond [18F]FDG for use in oncology and neurosciences. Nuclear medicine and biology. 2010; 37:727-740.
Dvorakova et al., Inhibitor-Decorated Polymer Conjugates Targeting Fibroblast Activation Protein. J Med Chem. 2017;60:8385-8393.
Edosada et al., Peptide substrate profiling defines fibroblast activation protein as an endopeptidase of strict Gly(2)-Pro(1)-cleaving specificity. FEBS Lett. Mar. 6, 2006;580(6):1581-6.
Extended EP Search Report for EP 18871298.8, mailed May 20, 2021, 7 pages.

(Continued)

Primary Examiner — Michael G. Hartley
Assistant Examiner — Melissa J Perreira
(74) Attorney, Agent, or Firm — Casimir Jones, SC; Jeffrey W. Childers

(57) ABSTRACT

Imaging and radiotherapeutics agents targeting fibroblast-activation protein-α (FAP-α) and their use in imaging and treating FAP-α related diseases and disorders are disclosed.

4 Claims, 9 Drawing Sheets
(4 of 9 Drawing Sheet(s) Filed in Color)

(56) References Cited

OTHER PUBLICATIONS

Ferreira et al., "Monitoring Alcoholic Fermentation: An Untargeted Approach". Journal of Agricultural and Food Chemistry, 2014,62, 6784-6793.
Fischer et al., Radioimmunotherapy of fibroblast activation protein positive tumors by rapidly internalizing antibodies. Clin Cancer Res. 2012;18:6208-6218.
Franco et al., Cancer associated fibroblasts in cancer pathogenesis. Semin Cell Dev Biol. Feb. 2010;21(1):33-9.
Garin-Chesa et al., Cell surface glycoprotein of reactive stromal fibroblasts as a potential antibody target in human epithelial cancers. Proc Natl Acad Sci U S A. Sep. 1990;87(18):7235-9. PMCID: PMC54718.
International Search Report and Written Opinion for PCT/US2018/057086, mailed May 10, 2019, 12 pages.
Jamous et al., Synthesis of peptide radiopharmaceuticals for the therapy and diagnosis of tumor diseases. Molecules. Mar. 14, 2013;18(3):3379-409.
Jansen et al., Extended structure-activity relationship and pharmacokinetic investigation of (4-quinolinoyl)glycyl-2-cyanopyrrolidine inhibitors of fibroblast activation protein (FAP). J Med Chem. Apr. 10, 2014;57(7):3053-74.
Jansen et al., Selective Inhibitors of Fibroblast Activation Protein (FAP) with a (4-Quinolinoyl)-glycyl-2-cyanopyrrolidine Scaffold. ACS Med Chem Lett. Mar. 18, 2013;4(5):491-6.
Kelly, Fibroblast activation protein-alpha and dipeptidyl peptidase IV (CD26): cell-surface proteases that activate cell signaling and are potential targets for cancer therapy. Drug Resist Updat. Feb.-Apr. 2005;8(1-2):51-8.
Kraman et al., Suppression of antitumor immunity by stromal cells expressing fibroblast activation protein-alpha. Science. Nov. 5, 2010;330(6005):827-30.
Laverman et al., Immuno-PET and Immuno-SPECT of Rheumatoid Arthritis with Radiolabeled Anti-Fibroblast Activation Protein Antibody Correlates with Severity of Arthritis. J Nucl Med. May 2015;56(5):778-83.
Li et al., Activatable Near-Infrared Fluorescent Probe for In Vivo Imaging of Fibroblast Activation Protein-alpha. Bioconjugate Chem. Jul. 19, 2012;23:1704-11.
Llewellyn et al., "Using community metabolomics as a new approach to discriminate marine microbial particulate organic matter in the western English Channel". Progress in Oceanography, vol. 137, Part B, Sep. 2015, p. 421-433.
Lo et al., Photodynamic molecular beacon triggered by fibroblast activation protein on cancer-associated fibroblasts for diagnosis and treatment of epithelial cancers. J Med Chem. Jan. 22, 2009;52(2):358-68.
Meletta et al., "Evaluation of the radiolabeled boronic acid-based FAP inhibitor MIP-1232 for atherosclerotic plaque imaging". Molecules, Jan. 27, 2015;20(2):2081-99.
Metabolomics—EMBL-EBI,ht , ://www.ebi.ac.ukitraininalonlineicaffsesimetabolornics- introduction/what-isisrnall-molecules/, retrieved on Dec. 12, 2023.5 pages.
Poplawski et al., Identification of selective and potent inhibitors of fibroblast activation protein and prolyl oligopeptidase. J Med Chem. May 9, 2013;56(9):3467-77.
Reilly et al., Advancing Novel Molecular Imaging Agents from Preclinical Studies to First-in-Humans Phase I Clinical Trials in Academia—A Roadmap for Overcoming Perceived Barriers. Bioconjugate chemistry. 2015; 26:625-632.
Rettig et al., Regulation and heteromeric structure of the fibroblast activation protein in normal and transformed cells of mesenchymal and neuroectodermal origin Cancer Res. Jul. 15, 1993;53(14):3327-35.
Ryabtsova et al., Acylated Gly-(2-cyano)pyrrolidines as inhibitors of fibroblast activation protein (FAP) and the issue of FAP/prolyl oligopeptidase (PREP)-selectivity. Bioorg Med Chem Lett. May 15, 2012;22(10):3412-7.
Scanlan et al., Molecular cloning of fibroblast activation protein alpha, a member of the serine protease family selectively expressed in stromal fibroblasts of epithelial cancers. Proc Natl Acad Sci U S A. Jun. 7, 1994;91(12):5657-61.
Scott et al., A Phase I dose-escalation study of sibrotuzumab in patients with advanced or metastatic fibroblast activation protein-positive cancer. Clin Cancer Res. May 2003;9(5):1639-47.
Tahtis et al., Expression and Targeting of Human Fibroblast Activation Protien in a Human Skin/Severe Combined Immunodeficient Mouse Breast Cancer Xenograft Model. Mol. Cancer Therap. Aug. 2003, vol. 2: 729-737.
Terry et al., Monitoring Therapy Response of Expiremental Arthritis with Radiolabeled Tracers Targeting Fibroblasts, Macrophages, or Integrin $\alpha v\beta 3$. J. Nucl. Med. Mar. 2016, 57(3): 467-472.
Third Party Observations for application No. EP18871298.8 Dated Jan. 10, 2024. 553 pages.
Third Party Observations for application No. EP20180871298. Dated Apr. 3, 2022. 7 pages.
Third Party Observations Japanese Patent Application No. 2020-523010. Dated Oct. 24, 2022. 7 pages.
Third Party Preissuance Submission filed in U.S. Appl. No. 16/758,182, filed Feb. 23, 2022, 6 pages.
Tsai et al., Substituted 4-carboxymethylpyroglutamic acid diamides as potent and selective inhibitors of fibroblast activation protein. J Med Chem. Sep. 23, 2010;53(18):6572-83.
Tuxhorn et al., Reactive stroma in human prostate cancer: induction of myofibroblast phenotype and extracellular matrix remodeling. Clin Cancer Res. Sep. 2002;8(9):2912-23.
Welt et al., Antibody targeting in metastatic colon cancer: a phase I study of monoclonal antibody F19 against a cell-surface protein of reactive tumor stromal fibroblasts. J Clin Oncol. Jun. 1994;12(6):1193-203.
Youn et al., In vivo noninvasive small animal molecular imaging. Osong Public Health Res Perspect. 2012; 3 :48-59.
Yu et al., The dipeptidyl peptidase IV family in cancer and cell biology. FEBS J. Mar. 2010;277(5):1126-44.

| | 5 min (n=3) | 0.5 h (n=4) | 2 h (n=3) | 6 hr (n=4) | 6 h - blocking (n=4) | 12 h (n=4) |
|---|---|---|---|---|---|---|
| blood | 15.13 ± 0.62 | 10.64 ± 1.54 | 4.10 ± 0.39 | 2.01 ± 0.18 | 0.02 ± 0.001 | 0.42 ± 0.04 |
| heart | 6.68 ± 0.99 | 4.98 ± 0.71 | 2.61 ± 0.09 | 1.07 ± 0.09 | 0.02 ± 0.002 | 0.46 ± 0.04 |
| lungs | 6.99 ± 1.37 | 5.60 ± 0.89 | 2.59 ± 0.32 | 1.36 ± 0.13 | 0.04 ± 0.006 | 0.39 ± 0.03 |
| liver | 6.32 ± 0.77 | 4.90 ± 0.59 | 2.98 ± 0.09 | 2.51 ± 0.09 | 0.33 ± 0.058 | 1.66 ± 0.22 |
| stomach | 3.28 ± 0.46 | 2.62 ± 0.20 | 1.69 ± 0.14 | 1.19 ± 0.15 | 0.06 ± 0.032 | 0.34 ± 0.05 |
| pancreas | 14.54 ± 1.66 | 12.14 ± 2.85 | 8.11 ± 0.34 | 3.28 ± 0.27 | 0.03 ± 0.005 | 1.15 ± 0.52 |
| spleen | 2.93 ± 0.25 | 2.46 ± 0.47 | 1.77 ± 0.27 | 1.54 ± 0.19 | 0.06 ± 0.008 | 1.10 ± 0.13 |
| fat | 0.74 ± 0.09 | 0.73 ± 0.13 | 0.61 ± 0.19 | 0.45 ± 0.16 | 0.02 ± 0.017 | 0.15 ± 0.08 |
| kidney | 4.60 ± 0.57 | 3.56 ± 0.18 | 1.95 ± 0.06 | 1.79 ± 0.21 | 1.16 ± 0.158 | 0.73 ± 0.05 |
| sm. int. | 6.80 ± 1.97 | 8.41 ± 1.35 | 3.64 ± 0.45 | 1.66 ± 0.22 | 0.09 ± 0.052 | 0.76 ± 0.14 |
| lrg. int. | 4.67 ± 0.42 | 4.57 ± 0.57 | 2.98 ± 0.27 | 1.97 ± 0.47 | 0.36 ± 0.342 | 0.55 ± 0.04 |
| bladder | 2.96 ± 0.95 | 13.60 ± 8.80 | 8.94 ± 6.48 | 3.41 ± 0.84 | 1.04 ± 0.466 | 2.25 ± 0.57 |
| muscle | 3.00 ± 0.22 | 3.53 ± 0.16 | 2.80 ± 0.07 | 1.79 ± 0.15 | 0.02 ± 0.005 | 0.60 ± 0.03 |
| femur | 4.76 ± 0.12 | 5.83 ± 0.72 | 4.95 ± 0.60 | 3.91 ± 0.70 | 0.08 ± 0.021 | 1.38 ± 0.20 |
| U87 | 9.71 ± 0.24[a] | 12.89 ± 1.45[a] | 12.28 ± 1.95[a] | 11.20 ± 1.03[a] | 0.27 ± 0.019[a] | 4.57 ± 0.54[a] |
| PC3 | 2.20 ± 0.20 | 3.10 ± 0.67 | 2.75 ± 0.11 | 3.40 ± 0.34 | 0.11 ± 0.024[a] | 0.95 ± 0.06 |
| U87:PC3 | 4.43 ± 0.31 | 4.23 ± 0.72 | 4.46 ± 0.62 | 3.30 ± 0.14 | 2.61 ± 0.440 | 4.82 ± 0.28 |
| U87:blood | 0.64 ± 0.04 | 1.22 ± 0.07 | 3.00 ± 0.38 | 5.56 ± 0.36 | 18.07 ± 1.197 | 10.94 ± 0.93 |
| U87:mm | 3.25 ± 0.26 | 3.66 ± 0.44 | 4.38 ± 0.66 | 6.29 ± 0.62 | 11.81 ± 2.086 | 7.69 ± 0.97 |

*Fig. 4*

IMAGING AND RADIOTHERAPEUTICS AGENTS TARGETING FIBROBLAST-ACTIVATION PROTEIN-α (FAP-α)

CROSS-REFERENCE TO RELATED APPLICATIONS

This application is a continuation of U.S. patent application Ser. No. 18/354,282, filed Jul. 18, 2023, which is continuation of U.S. patent application Ser. No. 16/758,182, filed Apr. 22, 2020, which is a U.S. § 371 National Entry Application of PCT/US2018/057086, filed Oct. 23, 2018, which claims the benefit of U.S. Provisional Application No. 62/575,607, filed Oct. 23, 2017, each of which is incorporated herein by reference in its entirety.

FEDERALLY SPONSORED RESEARCH OR DEVELOPMENT

This invention was made with government support under CA197470 awarded by the National Institutes of Health. The government has certain rights in the invention.

BACKGROUND

Fibroblast-activation protein-α (FAP-α) expression has been detected on the surface of fibroblasts in the stroma surrounding >90% of the epithelial cancers examined, including malignant breast, colorectal, skin, prostate and pancreatic cancers. (Garin-Chesa, et al., 1990; Rettig, et al., 1993; Tuxhorn, et al., 2002; Scanlan, et al., 1994). It is a characteristic marker for carcinoma-associated-fibroblast (CAF), which plays a critical role in promoting angiogenesis, proliferation, invasion, and inhibition of tumor cell death. (Allinen, et al., 2004; Franco, et al., 2010). In healthy adult tissues, FAP-α expression is only limited to areas of tissue remodeling or wound healing. (Scanlan, et al., 1994; Yu, et al., 2010; Bae, et al., 2008; Kraman, et al., 2010). In addition, FAP-α-positive cells are observed during embryogenesis in areas of chronic inflammation, arthritis, and fibrosis, as well as in soft tissue and bone sarcomas. (Scanlan, et al., 1994; Yu, et al., 2010). These characteristics make FAP-α a potential imaging and radiotherapeutic target for cancer and inflammation diseases.

Because FAP-α is expressed in tumor stroma, anti-FAP antibodies have been investigated for radioimmunotargeting of malignancies, including murine F19, sibrotuzumab (a humanized version of the F19 antibody), ESC11, ESC14, and others. (Welt, et al., 1994; Scott, et al., 2003; Fischer, et al., 2012). Antibodies also demonstrated the feasibility of imaging inflammation, such as rheumatoid arthritis. (Laverman, et al., 2015). The use of antibodies as molecular imaging agents, however, suffers from pharmacokinetic limitations, including slow blood and non-target tissue clearance (normally 2-5 days or longer) and non-specific organ uptake. Low molecular weight (LMW) agents demonstrate faster pharmacokinetics and a higher specific signal within clinically convenient times after administration. They also can be synthesized in radiolabeled form more easily and may offer a shorter path to regulatory approval. (Coenen, et al., 2010; Coenen, et al., 2012; Reilly, et al., 2015). To date, however, no LMW ligand has been reported with ideal properties for nuclear imaging of FAP-α.

SUMMARY

In some aspects, the presently disclosed subject matter provides a compound of Formula (I):

B-L-A     (I)

wherein: A is a targeting moiety for FAP-α; B is any optical or radiolabeled functional group suitable for optical imaging, PET imaging, SPECT imaging, or radiotherapy; and L is a linker having bi-functionalization adapted to form a chemical bond with B and A.

In particular aspects, A is an FAP-α targeting moiety having the structure of:

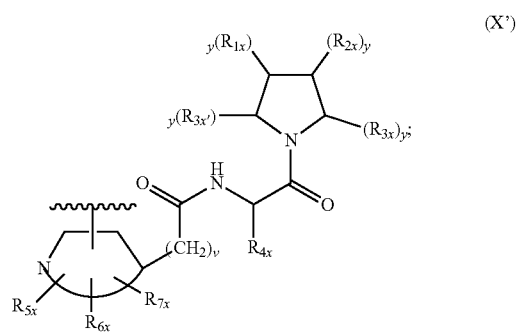

wherein each y is independently an integer selected from the group consisting of 0, 1, and 2; $R_{1x}$, $R_{2x}$, and $R_{3x'}$ are each independently selected from the group consisting of H, OH, halogen, $C_{1-6}$alkyl, —O—$C_{1-6}$alkyl, and —S—$C_{1-6}$alkyl; $R_{3x}$ is selected from the group consisting of H, —CN, —B(OH)$_2$, —C(O)alkyl, —C(O)aryl-, —C=C—C(O)aryl, —C=C—S(O)$_2$aryl, —CO$_2$H, —SO$_3$H, —SO$_2$NH$_2$, —PO$_3$H$_2$, and 5-tetrazolyl; $R_{4x}$ is H; $R_{5x}$, $R_{6x}$, and $R_{7x}$ are each independently selected from the group consisting of H, —OH, oxo, halogen, —$C_{1-6}$alkyl, —O—$C_{1-6}$alkyl, —S—$C_{1-6}$alkyl, —NR$_{8x}$R$_{9x}$, —OR$_{12x}$, -Het$_2$ and —Ar$_2$; each of $C_{1-6}$alkyl being optionally substituted with from 1 to 3 substituents selected from —OH and halogen; $R_{8x}$, $R_{9x}$, and $R_{12x}$ are each independently selected from the group consisting of H, —OH, halo, —$C_{1-6}$alkyl, —O—$C_{1-6}$alkyl, —S—$C_{1-6}$alkyl, and —Ar$_3$; $R_{10x}$, $R_{11x}$, $R_{13x}$ and $R_{14x}$ are each independently selected from the group consisting of H, —OH, halogen, —$C_{1-6}$alkyl, —O—$C_{1-6}$alkyl, and —S—$C_{1-6}$alkyl; Ar$_1$, Ar$_2$ and Ar$_3$ are each independently a 5- or 6-membered aromatic monocycle optionally comprising 1 or 2 heteroatoms selected from O, N and S; each of Ar$_1$, Ar$_2$ and Ar$_3$ being optionally and independently substituted with from 1 to 3 substituents selected from —NR$_{10x}$R$_{11x}$, —$C_{1-6}$alkyl, —O—$C_{1-6}$alkyl, and —S—$C_{16}$alkyl; Het$_2$ is a 5- or 6-membered non-aromatic monocycle optionally comprising 1 or 2 heteroatoms selected from O, N and S; Het$_2$ being optionally substituted with from 1 to 3 substituents selected from —NR$_{13x}$R$_{14x}$, —$C_{1-6}$alkyl, —O—$C_{1-6}$alkyl, and —S—$C_{1-6}$alkyl; v is 0, 1, 2, or 3; and

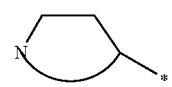

represents a 5 to 10-membered N-containing aromatic or non-aromatic mono- or bicyclic heterocycle, said heterocycle optionally further comprising 1, 2 or 3 heteroatoms selected from O, N and S; wherein

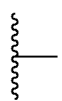

indicates a point of attachment of the FAP-α binding ligand to the linker, L, or the reporter moiety, B, wherein the point of attachment can be through any of the carbon atoms of the 5 to 10-membered N-containing aromatic or non-aromatic mono- or bicyclic heterocycle thereof; and stereoisomers and pharmaceutically acceptable salts thereof.

In more particular aspects, A is an FAP-α targeting moiety having the structure of:

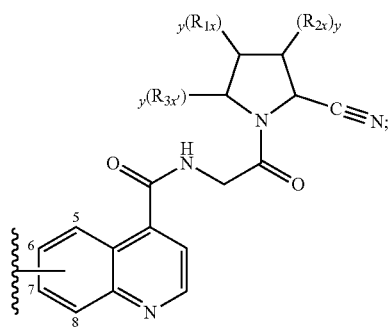

wherein

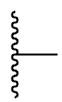

indicates a point or attachment of the FAP-α binding ligand to the linker, L, or the reporter moiety, B, wherein the point of attachment can be through any of carbon atoms 5, 6, 7, or 8 of the quinolinyl ring thereof; and stereoisomers and pharmaceutically acceptable salts thereof.

In yet more particular aspects, A is selected from the group consisting of:

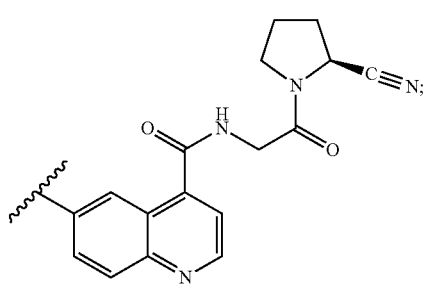

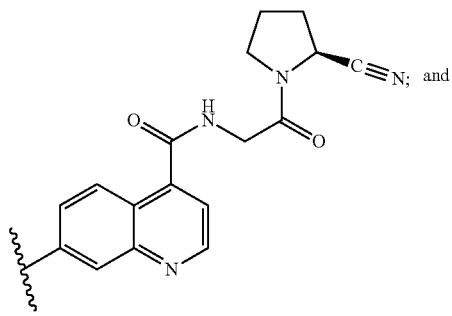

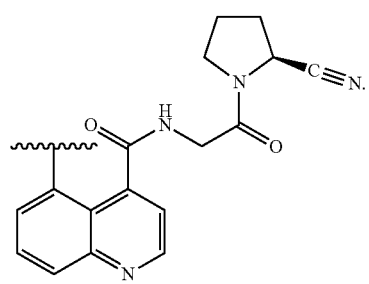

In other aspects, the presently disclosed subject matter provides a pharmaceutical composition comprising a compound of formula (I).

In some aspects, the presently disclosed subject matter provides a method for imaging a disease or disorder associated with fibroblast-activation protein-α (FAP-α), the method comprising administering a compound of formula (I), wherein the compound of formula (I) comprises an optical or radiolabeled functional group suitable for optical imaging, PET imaging, or SPECT imaging; and obtaining an image.

In other aspects, the presently disclosed subject matter provides a method for inhibiting fibroblast-activation protein-α (FAP-α), the method comprising administering to a subject in need thereof an effective amount of a compound of formula (I).

In yet other aspects, the presently disclosed subject matter provides a method for treating a fibroblast-activation protein-α (FAP-α)-related disease or disorder, the method comprising administering to a subject in need of treatment thereof an effective amount of a compound of formula (I), wherein the compound of formula (I) comprises a radiolabeled functional group suitable for radiotherapy.

In certain aspects, the (FAP-α)-related disease or disorder is selected from the group consisting of a proliferative disease, including, but not limited to, breast cancer, colorectal cancer, ovarian cancer, prostate cancer, pancreatic cancer, kidney cancer, lung cancer, melanoma, fibrosarcoma, bone and connective tissue sarcomas, renal cell carcinoma, giant cell carcinoma, squamous cell carcinoma, and adenocarcinoma; diseases characterized by tissue remodeling and/or chronic inflammation; disorders involving endocrinological dysfunction; and blood clotting disorders.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

The patent or application file contains at least one drawing executed in color. Copies of this patent or patent application publication with color drawings will be provided by the Office upon request and payment of the necessary fee.

Figure 1A:
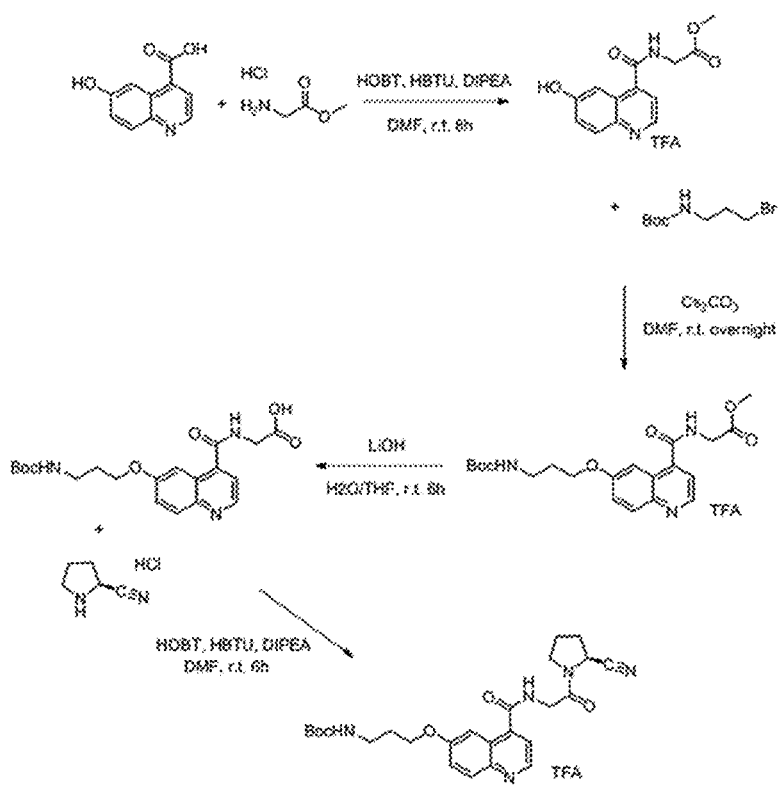
Figure 1B:
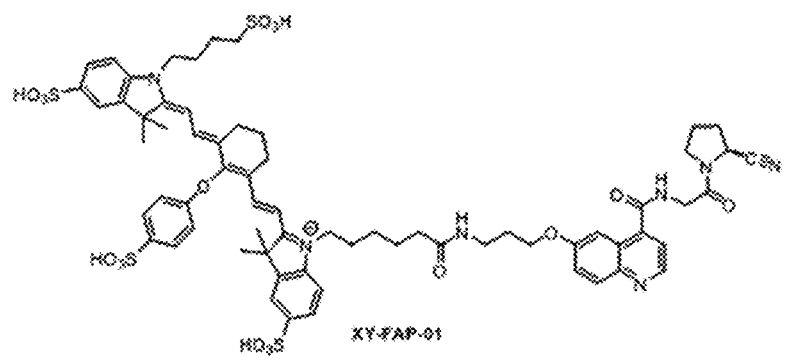
Figure 1C:
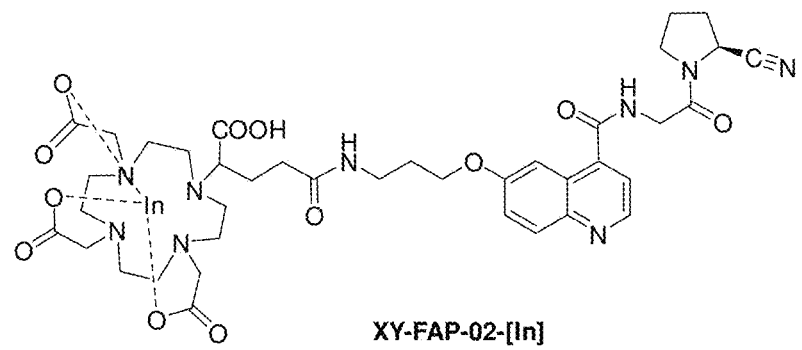
Figure 2:
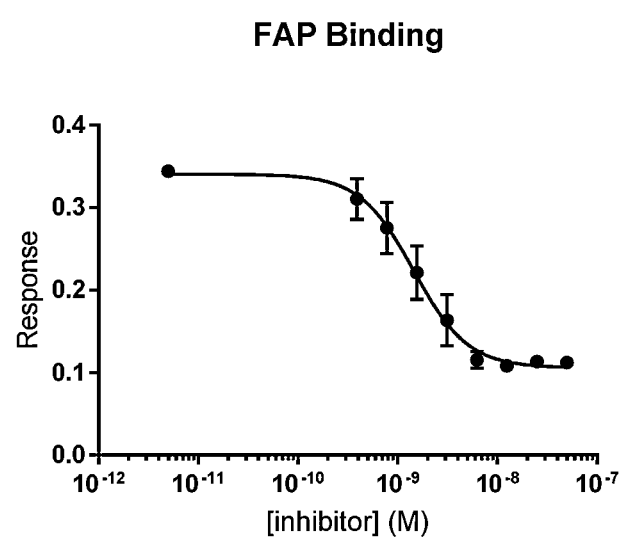
Figure 3A:
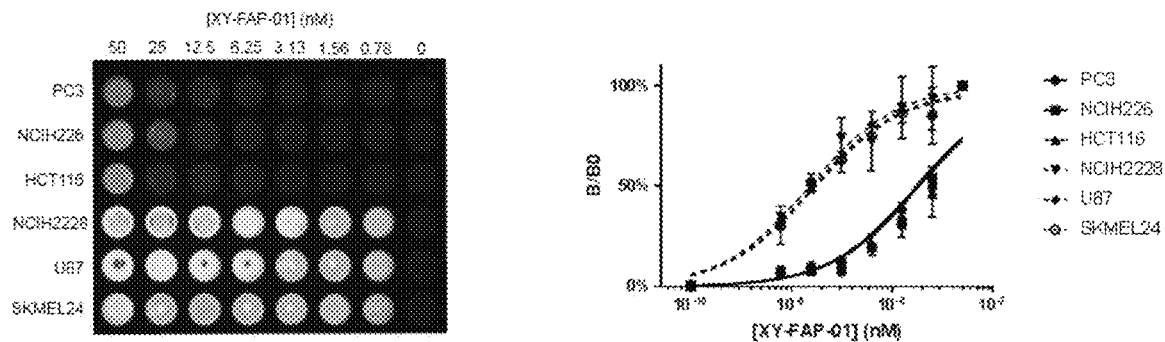
Figure 3B:
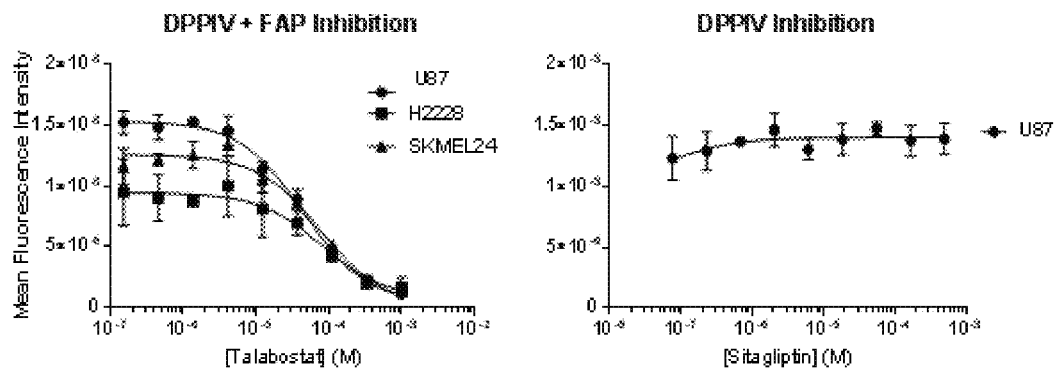
Figure 3C:
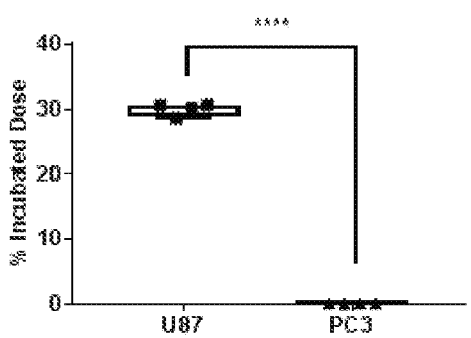
Figure 5A:
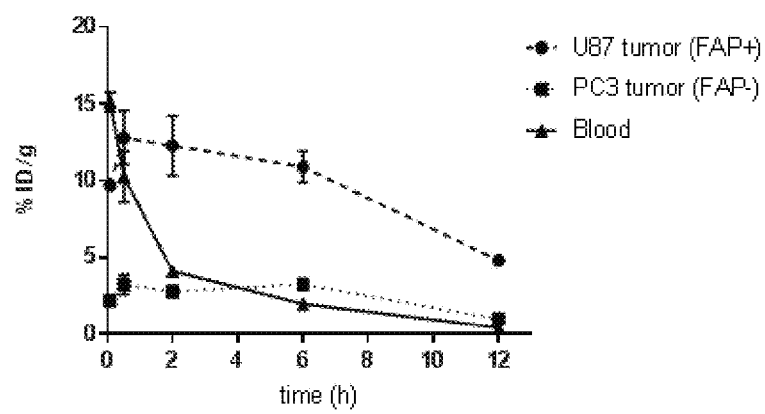
Figure 5B:
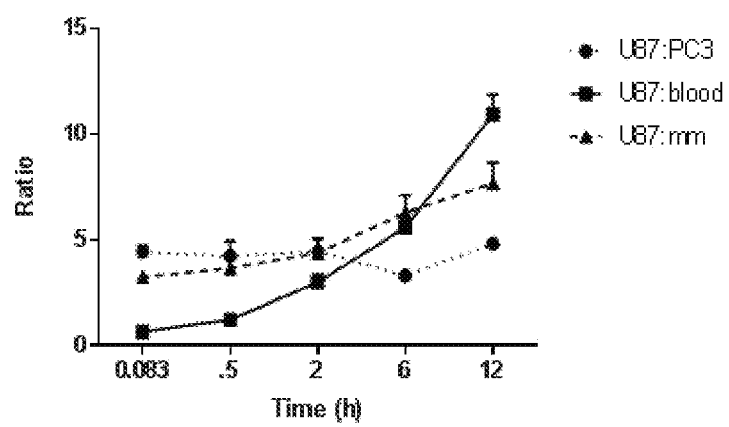
Figure 6:
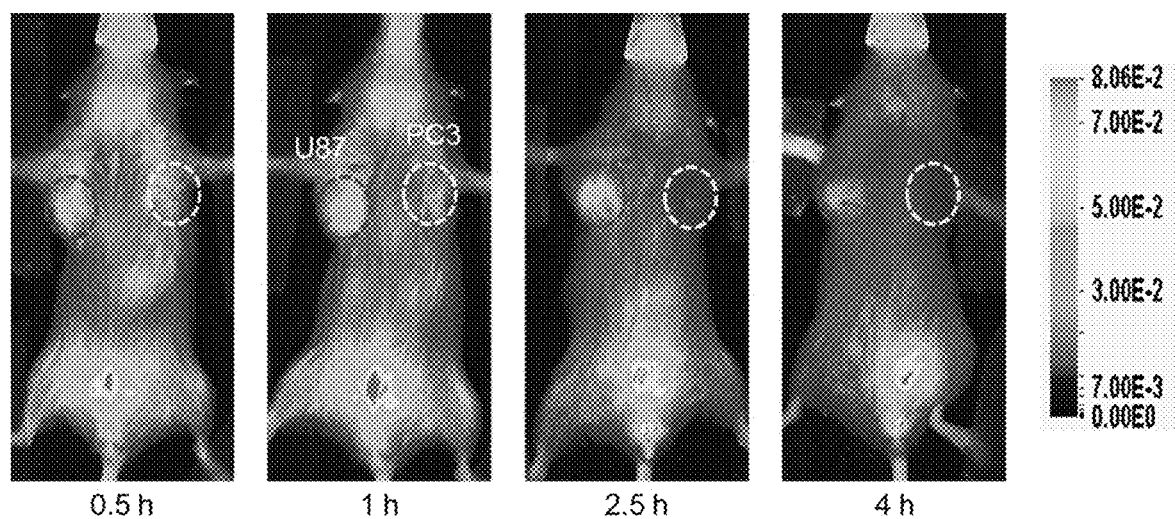
Figure 7:
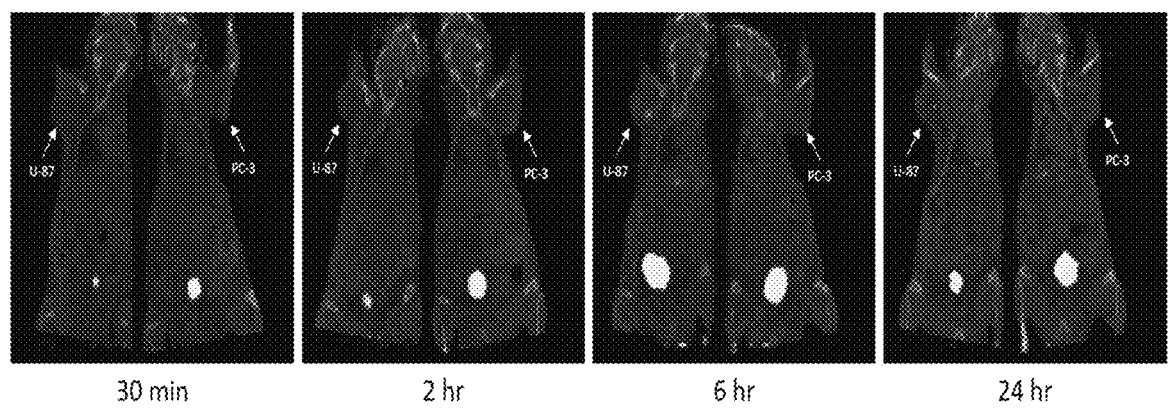
Figure 8:
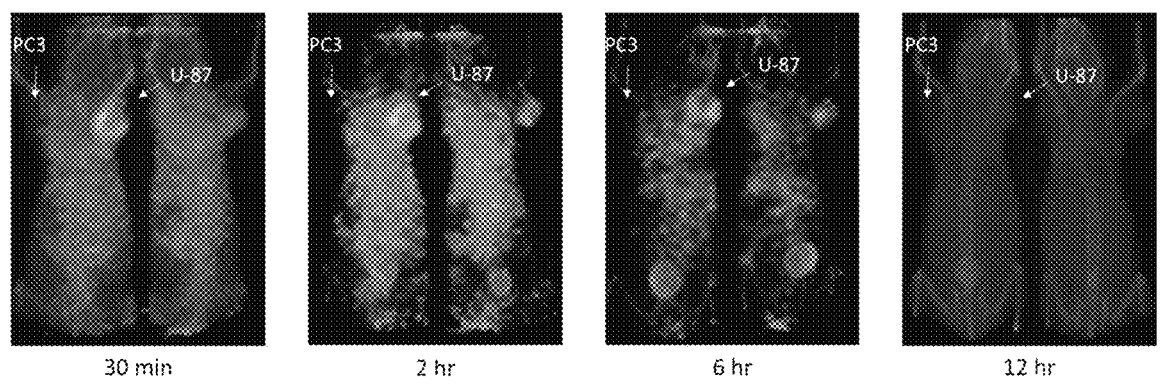

Having thus described the presently disclosed subject matter in general terms, reference will now be made to the accompanying Figures, which are not necessarily drawn to scale, and wherein:

FIG. 1A, FIG. 1B, and FIG. 1C show the synthetic pathway and structures of representative FAP-targeted agents, XY-FAP-01 and [$^{111}$In]-XY-FAP-02. FIG. 1A shows the multi-step synthesis of the ligand precursor, tert-butyl(S)-(3-((4-((2-(2-cyanopyrrolidin-1-yl)-2-oxoethyl)carbamoyl)quinolin-6-yl)oxy)propyl)carbamate. After each step, the reaction mixture was loaded onto a 25-g C18 cartridge and purified with a MeCN/water/TFA gradient. Identity of intermediate products was confirmed with $^1$H NMR. FIG. 1B shows the full structure of optical imaging agent, XY-FAP-01. XY-FAP-01 was produced with a one step reaction between the precursor and IRDye800CW-NHS. The major product was obtained at a yield of 85% after purification with HPLC. FIG. 1C shows the full structure of the SPECT imaging agent, [$^{111}$In]-XY-FAP-02. First, the precursor was functionalized with DOTA via a one step reaction between the precursor and DOTA-GA(t-Bu)$_4$-NHS. Unlabeled product was purified via HPLC to produce XY-FAP-02. Subsequent radiolabeling with 111 In and HPLC purification resulted in the radiolabeled product, [$^{111}$In]-XY-FAP-02;

FIG. 2 shows the inhibitory activity of XY-FAP-01 on human recombinant FAP. The inhibitory activity of XY-FAP-01 was determined using a fluorogenic FAP assay kit. Enzymatic activity of human recombinant FAP on a native substrate was inhibited in a concentration dependent fashion by XY-FAP-01. Semi-log inhibitory curves of XY-FAP-01 activity were generated and the determined Ki value of XY-FAP-01 was 1.26 nM;

FIG. 3A, FIG. 3B, and FIG. 3C show the assessment of the in vitro binding ability and specificity of XY-FAP-01 and [$^{111}$In]-XY-FAP-02. FIG. 3A shows the concentration dependent uptake of XY-FAP-01 in various cell lines. Cells incubated with various concentrations (range: 50 nM to 0.78 nM) of XY-FAP-01 were imaged with the LI-COR Pearl Impulse Imager to assess uptake of agent in various FAP-positive and FAP-negative cell lines (left). Dose-response curves of XY-FAP-01 uptake in FAP-positive cell lines (NCIH2228, U87, and SKMEL24) and FAP-negative cell lines (PC3, NCIH226, and HCT116) were generated (right). FIG. 3B shows the inhibition of XY-FAP-01 uptake in FAP-positive cell-lines. Cells incubated with 25-nM XY-FAP-01 were incubated with various concentrations of either a DPPIV and FAP inhibitor, Talabostat, or a DPPIV-only inhibitor, Sitagliptin. Uptake of XY-FAP-01 was measured and semi-log inhibitor-response curves were generated for both Talabostat and Sitagliptin. FIG. 3C shows the uptake of [$^{111}$In]-XY-FAP-02 in FAP-positive U87 and FAP-negative PC3 cell lines. Cells were incubated with 1 μCi [$^{111}$In]-XY-FAP-02 and were washed with cold PBS. Radioactivity of the cell pellets was measured and normalized to the incubated dose;

FIG. 4 is a table showing the ex vivo tissue biodistribution of [$^{111}$In]-XY-FAP-01 in tumor bearing mice. At 5 min, 0.5 h, 2 h, 6 h, and 12 h after injection of 10 μCi [$^{111}$In]-XY-FAP-01, NOD/SKID mice bearing U87 and PC3 tumor xenografts were sacrificed and tissues were collected for biodistribution analysis. Additionally, mice co-injected with unlabeled XY-FAP-02 and 10 μCi [$^{111}$In]-XY-FAP-01 were sacrificed at 6 h post-injection to study the effect of blocking on uptake of the radiolabeled compound. Data presented as mean±standard deviation. $^a$Student's t test comparison of mean % ID/g of PC3 tumor versus U87 tumor demonstrated significant difference between the two groups at 5 min, 0.5 h, 2 h, and 6 h post injection (p<0.0001). No significant difference between the two groups were seen in the blocking study at 6 h. $^b$Student's t test comparison of mean % ID/g of PC3 tumor versus U87 tumor demonstrated significant difference between the two groups at 12 h post injection (p=0.0006). $^c$Student's t test comparing % ID/g between PC3 tumor and U87 tumors at 6 h post injection showed significant difference between % ID/g tumors in the blocking study at 6 h versus the normal biodistribution results at 6 h (p<0.0001);

FIG. 5A and FIG. 5B show the time-activity relationship of the ex vivo biodistribution of [$^{111}$In]-XY-FAP-02. FIG. 5A shows tissue time activity curves (TACs) of [$^{111}$In]-XY-FAP-02 activity in U87 tumor, PC3 tumor, and blood. FIG. 5B shows the ratios of % ID/g between U87 tumor and PC3 tumor, blood, and muscle (mm) versus time;

FIG. 6 shows serial NIRF-imaging of XY-FAP-01 in tumor bearing mice. NOD/SKID mice bearing FAP-positive U87 (yellow circle) and FAP-negative PC3 (red circle) tumor xenografts were injected with 10 nmol of XY-FAP-01 via the tail vein followed by serial NIRF-imaging on the LI-COR Pearl Impulse Imager. Representative images at 0.5 h, 1 h, 2.5 h, and 4 h after injection are shown;

FIG. 7 shows SPECT-CT images of [$^{111}$In]-XY-FAP-02 at 30 min, 2 h, 6 h, and 24 h after injection in NOD/SKID female mice bearing U87 and PC3 tumor xenografts in the upper flanks; and FIG. 8 show three-dimensional SPECT-CT images of [$^{111}$In]-XY-FAP-02 at 30 min, 2 h, 6 h, and 24 h after injection in NOD/SKID female mice bearing U87 and PC3 tumor xenografts in the upper flanks.

DETAILED DESCRIPTION

The presently disclosed subject matter now will be described more fully hereinafter with reference to the accompanying Figures, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

I. Imaging and Radiotherapeutics Agents Targeting Fibroblast-Activation Protein-α (Fap-α)

FAP-α is a type II integral membrane serine protease of the prolyl oligopeptidase family, which are distinguished by their ability to cleave the Pro-AA peptide bond (where AA represents any amino acid). It has been shown to play a role in cancer by modifying bioactive signaling peptides through this enzymatic activity (Kelly, et al., 2005; Edosada, et al., 2006). FAP-α expression has been detected on the surface of fibroblasts in the stroma surrounding greater than 90% of the epithelial cancers, including, but not limited to, malignant breast, colorectal, skin, prostate, pancreatic cancers, and the like, and inflammation diseases, including, but not limited to, arthritis, fibrosis, and the like, with nearly no expression in healthy tissues. Accordingly, imaging and radiotherapeutic agents specifically targeting FAP-α is of clinical importance.

FAP-α exists as a homodimer to carry out its enzymatic function. Inhibitors selectively targeting FAP-α has been reported (Lo, et al., 2009; Tsai, et al., 2010; Ryabtsova, et al., 2012; Poplawski, et al., 2013; Jansen, et al., 2013; Jansen, et al., 2014). The presently disclosed subject matter provides, in part, a FAP-α selective targeting moiety that can be modified with an optical dye, a radiometal chelation complex, and other radiolabeled prosthetic groups, thus providing a platform for the imaging and radiotherapy targeting FAP-α.

Radionuclide molecular imaging, including positron emission tomography (PET), is the most mature molecular imaging technique without tissue penetration limitations. Due to its advantages of high sensitivity and quantifiability, radionuclide molecular imaging plays an important role in clinical and preclinical research (Youn, et al., 2012; Chen, et al., 2014). Many radionuclides, primarily β- and alpha emitters, have been investigated for targeted radioimmunotherapy and include both radiohalogens and radiometals (see Table 1 for representative therapeutic radionuclides).

TABLE 1

Representative Therapeutic Radionuclides

| | |
|---|---|
| β-particle emitters | $^{90}$Y, $^{131}$I, $^{177}$Lu, $^{153}$Sm, $^{186}$Re, $^{188}$Re, $^{67}$Cu, $^{212}$Pb |
| α-particle emitters | $^{225}$Ac, $^{213}$Bi, $^{212}$Bi, $^{211}$At, $^{212}$Pb |
| Auger electron emitters | $^{125}$I, $^{123}$I, $^{67}$Ga, $^{111}$In |

The highly potent and specific binding moiety targeting FAP-α enables its use in nuclear imaging and radiotherapy. The presently disclosed subject matter provides the first synthesis of nuclear imaging and radiotherapy agents based on this dual-targeting moiety to FAP-α.

Accordingly, in some embodiments, the presently disclosed subject matter provides potent and selective low-molecular-weight (LMW) ligands of FAP-α, i.e., an FAP-α selective inhibitor, conjugated with a targeting moiety feasible for modification with optical dyes and radiolabeling groups, including metal chelators and metal complexes, which enable in vivo optical imaging, nuclear imaging (optical, PET and SPECT), and radiotherapy targeting FAP-α. Importantly, the presently disclosed compounds can be modified, e.g., conjugated with, labeling groups without significantly losing their potency. The presently disclosed approach allows for the convenient labeling of the FAP-α ligand with optical dyes and PET or SPECT isotopes, including, but not limited to, $^{68}$Ga, $^{64}$Cu, $^{18}$F, $^{86}$Y, $^{90}$Y, $^{89}$Zr, $^{111}$In, $^{99m}$Tc, $^{125}$I, $^{124}$I, for FAP-α related imaging applications. Further, the presently disclosed approach allows for the radiolabeling of the FAP-α ligand with radiotherapeutic isotopes, including but not limited to, $^{90}$Y, $^{177}$Lu, $^{125}$I, $^{131}$I, $^{211}$At, $^{111}$In, $^{153}$Sm, $^{186}$Re, $^{188}$Re, $^{67}$Cu, $^{212}$Pb, $^{225}$Ac, $^{213}$Bi, $^{212}$Bi, $^{212}$Pb, and $^{67}$Ga, for FAP-α related radio-therapy.

In a particular embodiment, an optical agent conjugated with IRDye-800CW (XY-FAP-01) was synthesized and showed selective uptake in vitro on a FAP-α+ U87 cell line and in vivo on a FAP-α+ U87 tumor and clearly detected the tumor. In another particular embodiment, an 111 In labeled ligand (XY-FAP-02-[$^{111}$In]) was successfully obtained in high yield and purity from its precursor with a metal chelator. The in vivo study showed clear tumor radiotracer uptake in mice bearing FAP-α-positive U87 tumors with minimum non-specific organ uptake, which allows the specific imaging of FAP-α expressing tumors. The presently disclosed FAP-α targeting moiety can be adapted for use with optical dyes and radioisotopes known in the art for imaging and therapeutic applications targeting FAP-α.

More particularly, in some embodiments, the presently disclosed subject matter provides a compound of the general structure of Formula (I):

B-L-A (I)

wherein: A is a targeting moiety for FAP-α; B is any optical or radiolabeled functional group suitable for optical imaging, positron-emission tomography (PET) imaging, single-photon emission computed tomography (SPECT) imaging, or radiotherapy; and L is a linker having bi-functionalization adapted to form a chemical bond with B and A.

Representative targeting moieties for FAP-α are disclosed in U.S. Patent Application Publication No. US2014/0357650 for Novel FAP Inhibitors to Jansen et al., published Dec. 4, 2014; U.S. Pat. No. 9,346,814 for Novel FAP Inhibitors to Jansen et al., issued May 24, 2016; and International PCT Patent Publication No. WO 2013/107820 for Novel FAP Inhibitors to Jansen et al., published Jul. 25, 2013, each of which are incorporate by reference in their entirety.

More particularly, U.S. Pat. No. 9,346,814 to Jansen et al., discloses FAP-α inhibitors of formula (X), or a stereoisomer, tautomer, racemate, salt, hydrate, or solvate thereof, which are suitable for use with the presently disclosed subject matter:

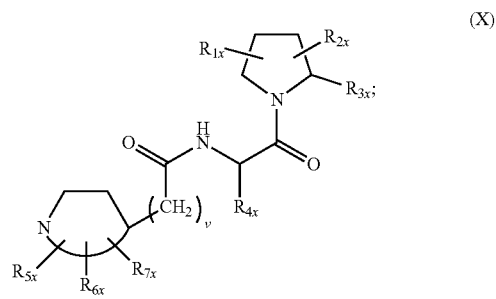

(X)

wherein:
$R_{1x}$ and $R_{2x}$ are each independently selected from the group consisting of H, OH, halogen, $C_{1-6}$alkyl, —O—$C_{1-6}$alkyl, and —S—$C_{1-6}$alkyl;
$R_{3x}$ is selected from the group consisting of H, —CN, —B(OH)$_2$, —C(O)alkyl, —C(O)aryl-, —C≡C—C(O)aryl, —C≡C—S(O)$_2$aryl, —CO$_2$H, —SO$_3$H, —SO$_2$NH$_2$, —PO$_3$H$_2$, and 5-tetrazolyl;
$R_{4x}$ is H;
$R_{5x}$, $R_{6x}$, and $R_{7x}$ are each independently selected from the group consisting of H, —OH, oxo, halogen, —C$_{1-6}$alkyl, —O—C$_{1-6}$alkyl, —S—C$_{1-6}$alkyl, —NR$_{8x}$R$_{9x}$, —OR$_{12x}$, -Het$_2$ and —Ar$_2$; each of C$_{1-6}$alkyl being optionally substituted with from 1 to 3 substituents selected from —OH and halogen;

$R_{8x}$, $R_{9x}$, and $R_{12x}$ are each independently selected from the group consisting of H, —OH, halo, —$C_{1-6}$alkyl, —O—$C_{1-6}$alkyl, —S—$C_{1-6}$alkyl, and —$Ar_3$;

$R_{10x}$, $R_{11x}$, $R_{13x}$ and $R_{14x}$ are each independently selected from the group consisting of H, —OH, halogen, —$C_{1-6}$alkyl, —O—$C_{1-6}$alkyl, and —S—$C_{1-6}$alkyl; $Ar_1$, $Ar_2$ and $Ar_3$ are each independently a 5- or 6-membered aromatic monocycle optionally comprising 1 or 2 heteroatoms selected from O, N and S; each of $Ar_1$, $Ar_2$ and $Ar_3$ being optionally and independently substituted with from 1 to 3 substituents selected from —$NR_{10x}R_{11x}$, —$C_{1-6}$alkyl, —O—$C_{1-6}$alkyl, and —S—$C_{1-6}$alkyl;

$Het_2$ is a 5- or 6-membered non-aromatic monocycle optionally comprising 1 or 2 heteroatoms selected from O, N and S; $Het_2$ being optionally substituted with from 1 to 3 substituents selected from —$NR_{13x}R_{14x}$, —$C_{1-6}$alkyl, —O—$C_{1-6}$alkyl, and —S—$C_1$-6alkyl;

v is 0, 1, 2, or 3; and

represents a 5 to 10-membered N-containing aromatic or non-aromatic mono- or bicyclic heterocycle, said heterocycle optionally further comprising 1, 2 or 3 heteroatoms selected from O, N and S.

In particular embodiments,

is selected from the group consisting of:

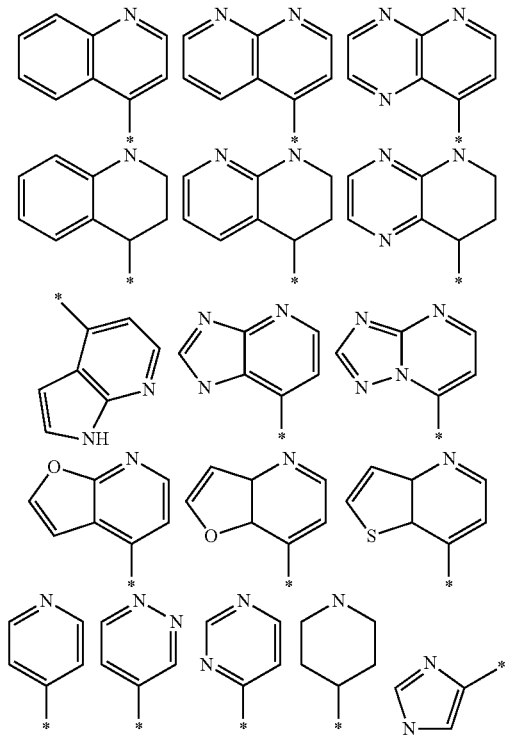

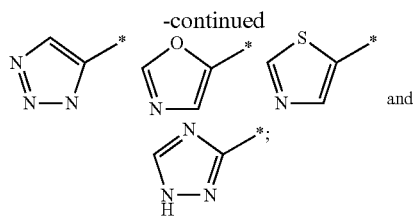

wherein * indicates the point of attachment of the 5 to 10-membered N-containing aromatic or non-aromatic mono- or bicyclic heterocycle to —$(CH_2)_v$—.

Accordingly, in some embodiments, A is an FAP-α targeting moiety having the structure of:

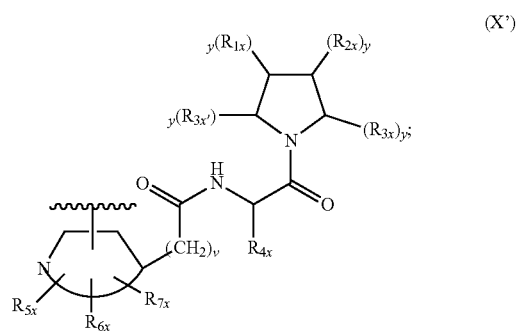

(X')

wherein each y is independently an integer selected from the group consisting of 0, 1, and 2;

$R_{1x}$, $R_{2x}$, and $R_{3x'}$, are each independently selected from the group consisting of H, OH, halogen, $C_{1-6}$alkyl, —O—$C_{1-6}$alkyl, and —S—$C_{1-6}$alkyl;

$R_{3x}$ is selected from the group consisting of H, —CN, —$B(OH)_2$, —C(O)alkyl, —C(O)aryl-, —C=C—C(O)aryl, —C=C—S(O)_2aryl, —$CO_2H$, —$SO_3H$, —$SO_2NH_2$, —$PO_3H_2$, and 5-tetrazolyl;

$R_{4x}$ is H;

$R_{5x}$, $R_{6x}$, and $R_{7x}$ are each independently selected from the group consisting of H, —OH, oxo, halogen, —$C_{1-6}$alkyl, —O—$C_{1-6}$alkyl, —S—$C_{1-6}$alkyl, —$NR_{8x}R_{9x}$, —$OR_{12x}$, -$Het_2$ and —$Ar_2$; each of $C_{1-6}$alkyl being optionally substituted with from 1 to 3 substituents selected from —OH and halogen;

$R_{8x}$, $R_{9x}$, and $R_{12x}$ are each independently selected from the group consisting of H, —OH, halo, —$C_{1-6}$alkyl, —O—$C_{1-6}$alkyl, —S—$C_{1-6}$alkyl, and —$Ar_3$;

$R_{10x}$, $R_{11x}$, $R_{13x}$ and $R_{14x}$ are each independently selected from the group consisting of H, —OH, halogen, —$C_{1-6}$alkyl, —O—$C_{1-6}$alkyl, and —S—$C_{1-6}$alkyl; $Ar_1$, $Ar_2$ and $Ar_3$ are each independently a 5- or 6-membered aromatic monocycle optionally comprising 1 or 2 heteroatoms selected from O, N and S; each of $Ar_1$, $Ar_2$ and $Ar_3$ being optionally and independently substituted with from 1 to 3 substituents selected from —$NR_{10x}R_{11x}$, —$C_{1-6}$alkyl, —O—$C_{1-6}$alkyl, and —S—$C_{1-6}$alkyl;

$Het_2$ is a 5- or 6-membered non-aromatic monocycle optionally comprising 1 or 2 heteroatoms selected from O, N and S; $Het_2$ being optionally substituted with from 1 to 3 substituents selected from —$NR_{13x}R_{14x}$, —$C_{1-6}$alkyl, —O—$C_{1-6}$alkyl, and —S—$C_{1-6}$alkyl;

v is 0, 1, 2, or 3; and

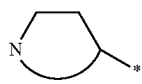 [SMILES: *CCCN]

represents a 5 to 10-membered N-containing aromatic or non-aromatic mono- or bicyclic heterocycle, said heterocycle optionally further comprising 1, 2 or 3 heteroatoms selected from O, N and S;

wherein

indicates a point of attachment of the FAP-α binding ligand to a linker, e.g., L, or a reporter moiety, such as an optical or radiolabeled functional group suitable for optical imaging, PET imaging, SPECT imaging or radiotherapy, wherein the point of attachment can be through any of the carbon atoms of the 5 to 10-membered N-containing aromatic or non-aromatic mono- or bicyclic heterocycle thereof; and stereoisomers and pharmaceutically acceptable salts thereof.

In particular embodiments,

is selected from the group consisting of:

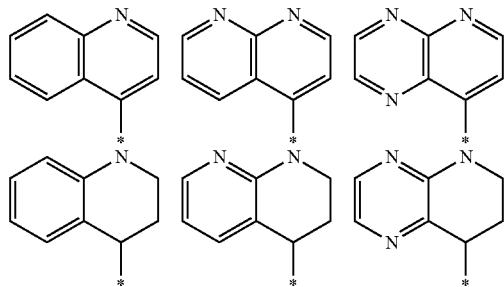

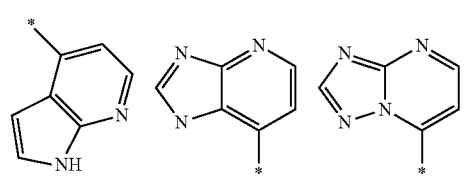

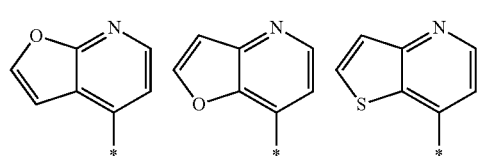

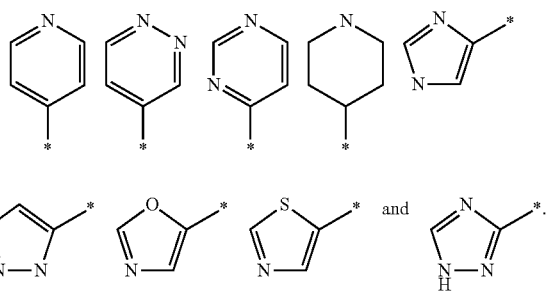

In some embodiments, A is an FAP-α targeting moiety having the structure of:

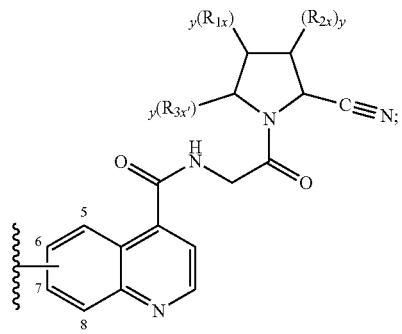

wherein y, $R_{1x}$, $R_{2x}$ and $R_{3x'}$ are defined as hereinabove;

indicates a point of attachment of the FAP-α binding ligand to a linker, e.g., L, or a reporter moiety, such as an optical or radiolabeled functional group suitable for optical imaging, PET imaging, SPECT imaging or radiotherapy, wherein the point of attachment can be through any of carbon atoms 5, 6, 7, or 8 of the quinolinyl ring thereof; and stereoisomers and pharmaceutically acceptable salts thereof.

In particular embodiments, A is selected from the group consisting of:

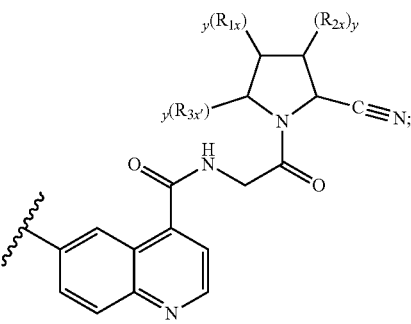

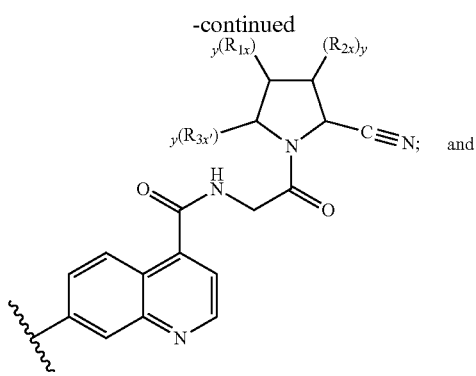
and
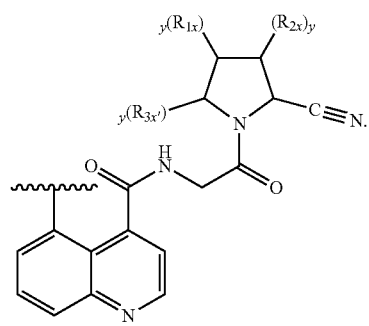
In more particular embodiments, A is selected from the group consisting of:
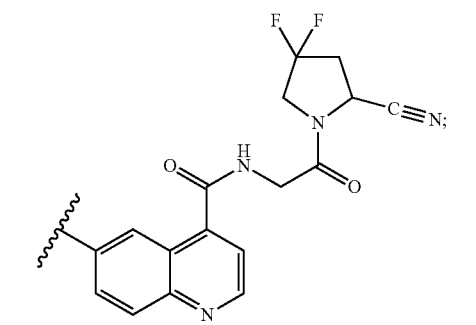
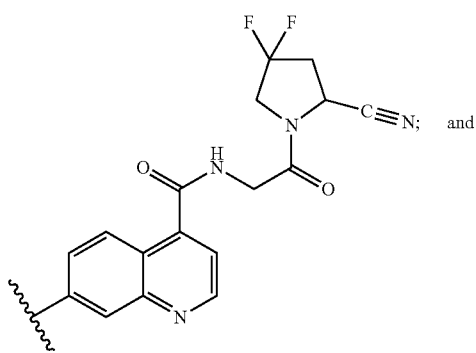
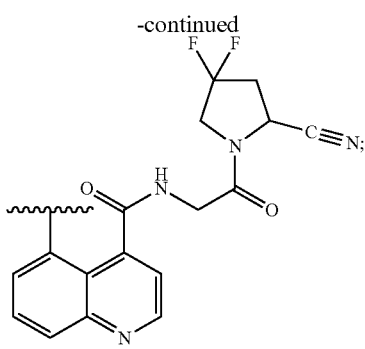
and stereoisomers thereof.
In yet more particular embodiments, A is selected from the group consisting of:
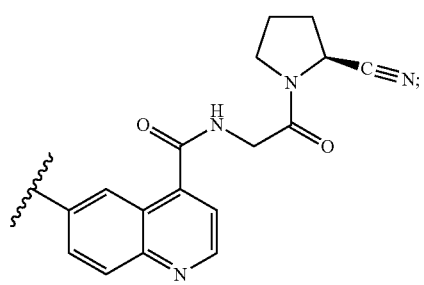
A1
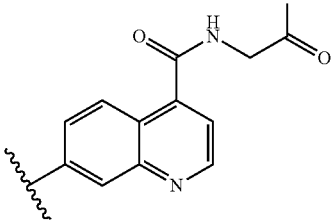
A2
and
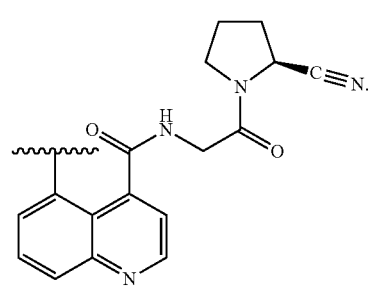
A3
In some embodiments, the combination of L and B can be represented by:
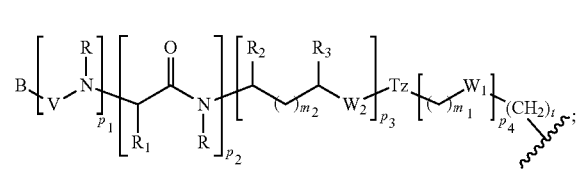

wherein the subunits associated with elements $p_1$, $p_2$, $p_3$ and $p_4$ may be in any order; t is an integer selected from the group consisting of 1, 2, 3, 4, 5, 6, 7, and 8; $p_1$, $p_3$, and $p_4$ are each independently 0 or 1; $p_2$ is an integer selected from the group consisting of 0, 1, 2, and 3, and when $p_2$ is 2 or 3, each $R_1$ is the same or different; $m_1$ and $m_2$ are each an integer independently selected from the group consisting of 0, 1, 2, 3, 4, 5, and 6; $W_1$ is selected from the group consisting of a bond, —S—, —C(=O)—NR—, and —NR—C(=O)—; $W_2$ is selected from the group consisting of a bond, —S—, —CH$_2$—C(=O)—NR—, —C(O)—, —NRC(O)—, —NR'C(O)NR—, —NRC(S)NR'$_2$—, —NRC(O)O—, —OC(O)NR—, —OC(O)—, —C(O)NR—, —NR—C(O)—, —C(O)O—, —(O—CH$_2$—CH$_2$)$_q$— and —(CH$_2$—CH$_2$—O)$_q$—, wherein q is selected from the group consisting of 1, 2, 3, 4, 5, 6, 7, and 8; each R or R' is independently H, alkyl, substituted alkyl, cycloalkyl, substituted cycloalkyl, heterocycloalkyl, substituted heterocycloalkyl, aryl, substituted aryl, heteroaryl, substituted heteroaryl, and —OR$_4$, wherein R$_4$ is selected from the group consisting of H, alkyl, substituted alkyl, cycloalkyl, substituted cycloalkyl, heterocycloalkyl, and substituted heterocycloalkyl, wherein q is defined as immediately hereinabove; Tz is a triazole group that can be present or absent and, if present, is selected from the group consisting of

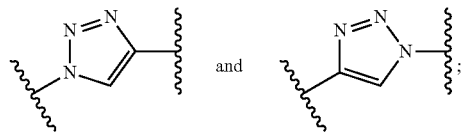 [SMILES: *c1cn(*)nn1 ; *c1cn(*)nn1]
and each $R_1$ is independently H, $C_1$-$C_6$ alkyl, $C_3$-$C_{12}$ aryl, —(CH$_2$)$_q$—$C_3$-$C_{12}$ aryl, —$C_4$-$C_{16}$ alkylaryl, or —(CH$_2$)$_q$-$C_4$-$C_{16}$ alkylaryl; $R_2$ and $R_3$ are each independently H and —CO$_2$R$_5$, wherein $R_5$ is selected from the group consisting of H, $C_1$-$C_6$ alkyl, $C_3$-$C_{12}$ aryl, and $C_4$-$C_{16}$ alkylaryl, wherein when one of $R_2$ or $R_3$ is CO$_2$R$_5$, then the other is H; V is selected from the group consisting of —C(O)—, —C(S)—, —NRC(O)—, —NRC(S)—, and —OC(O)—; B is any optical or radiolabeled functional group suitable for optical, PET, or SPECT imaging or radiotherapy; and stereoisomers and pharmaceutically acceptable salts thereof.

In some embodiments, L has the following general structure:

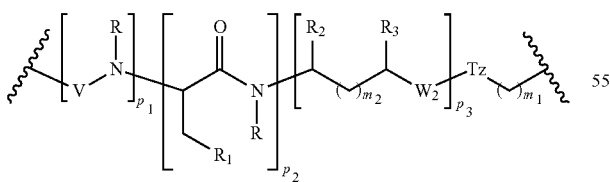

wherein $p_1$, $p_2$, $p_3$, $m_1$, $m_2$, q, t, Tz, $W_2$, R, $R_1$, $R_2$, $R_3$, and V are defined as hereinabove.

In some embodiments, L is selected from the group consisting of -$L_1$-, -$L_2$-$L_3$-, and -$L_1$-$L_2$-$L_3$-, wherein:

$L_1$ is —NR—(CH$_2$)$_q$—[O—CH$_2$—CH$_2$—O]$_q$—(CH$_2$)$_q$—C(=O)—;

$L_2$ is —NR—(CH$_2$)$_q$—C(COOR$_5$)—NR—; and $L_3$ is —(O=)C—(CH$_2$)$_q$—C(=O)—;

wherein each q is independently an integer selected from the group consisting of 1, 2, 3, 4, 5, 6, 7, and 8; and R and $R_5$ are as defined hereinabove.

In particular embodiments, L is:

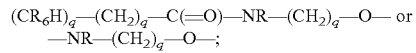

wherein each q and R is defined hereinabove; and $R_6$ is H or —COOR$_5$.

In yet more particular embodiments, L is selected from the group consisting of:

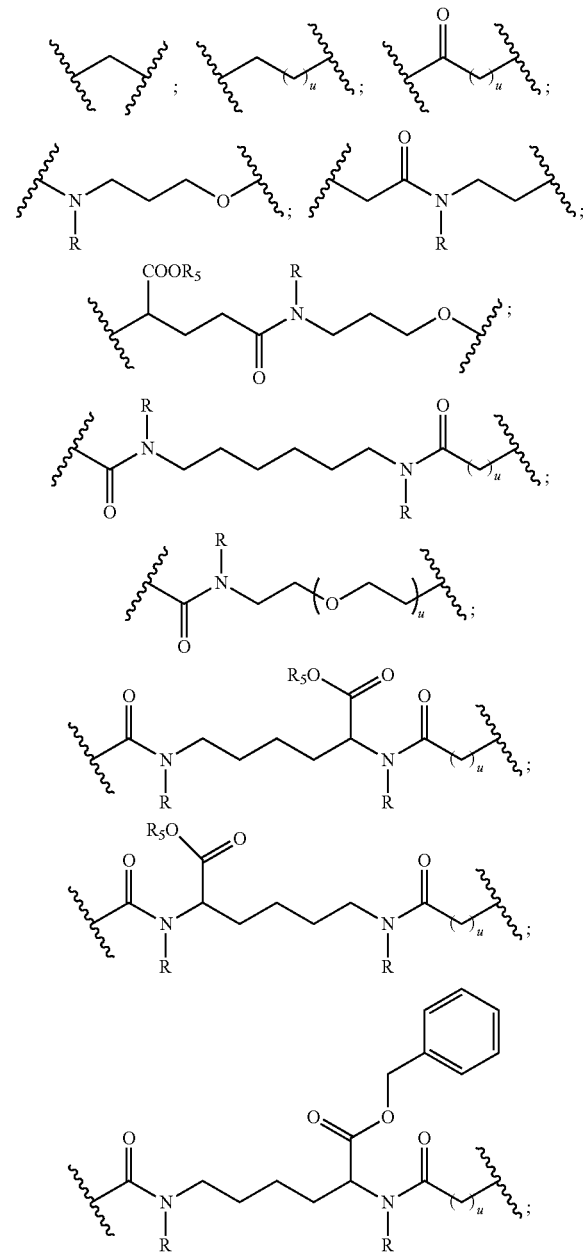

-continued

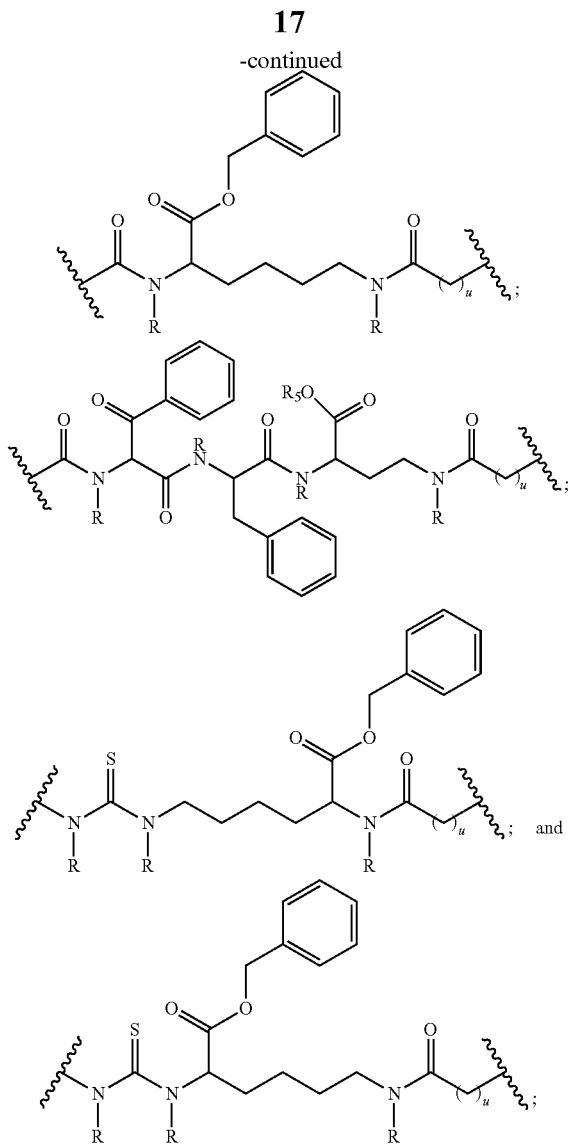

wherein u is an integer selected from 1, 2, 3, 4, 5, 6, 7, and 8; and R and $R_5$ are as defined hereinabove.

Suitable linkers are disclosed in U.S. Patent Application Publication No. US2011/0064657 A1, for "Labeled Inhibitors of Prostate Specific Membrane Antigen (PSMA), Biological Evaluation, and Use as Imaging Agents," published Mar. 17, 2011, to Pomper et al., and U.S. Patent Application Publication No. US2012/0009121 A1, for "PSMA-Targeting Compounds and Uses Thereof," published Jan. 12, 2012, to Pomper et al, each of which is incorporated by reference in its entirety.

In some embodiments, B is a radiolabeled prosthetic group comprising a radioisotope selected from the group consisting of $^{18}$F, $^{124}$I, $^{125}$I, $^{131}$I, and $^{211}$At. Representative radiolabeled prosthetic groups include, but are not limited to:

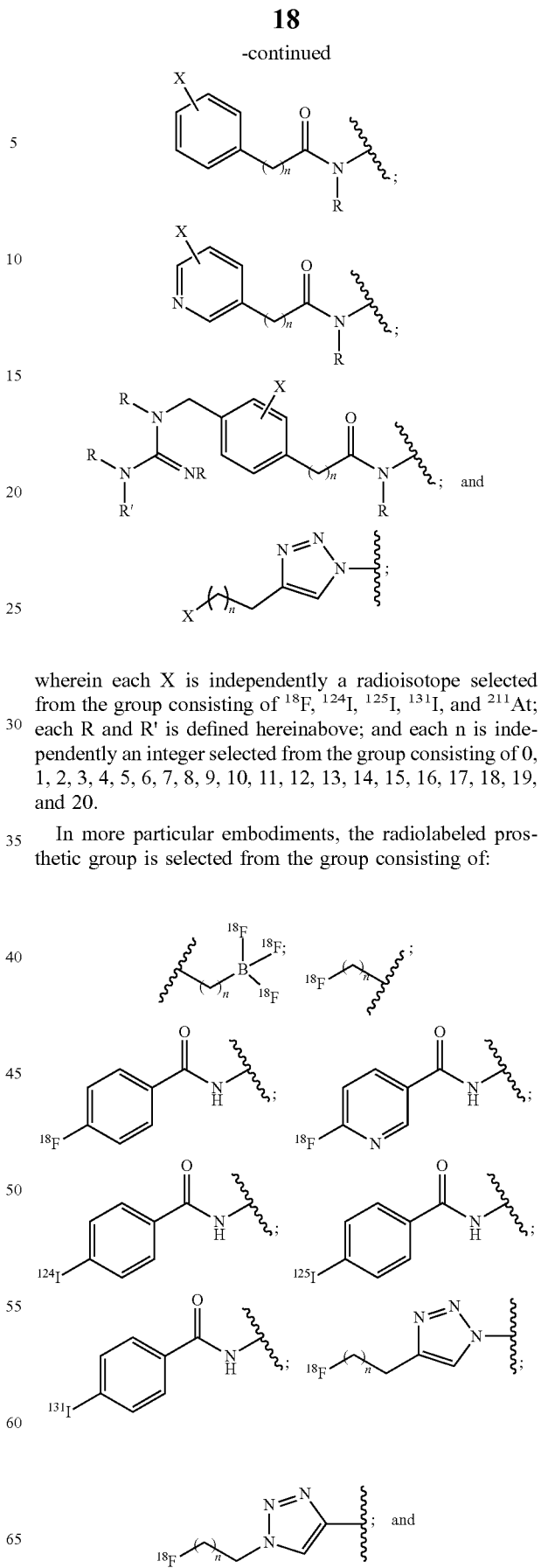

wherein each X is independently a radioisotope selected from the group consisting of $^{18}$F, $^{124}$I, $^{125}$I, $^{131}$I, and $^{211}$At; each R and R' is defined hereinabove; and each n is independently an integer selected from the group consisting of 0, 1, 2, 3, 4, 5, 6, 7, 8, 9, 10, 11, 12, 13, 14, 15, 16, 17, 18, 19, and 20.

In more particular embodiments, the radiolabeled prosthetic group is selected from the group consisting of:

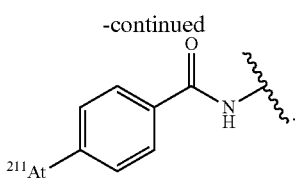
In other embodiments, B comprises a chelating agent. Representative chelating agents include, but are not limited to:
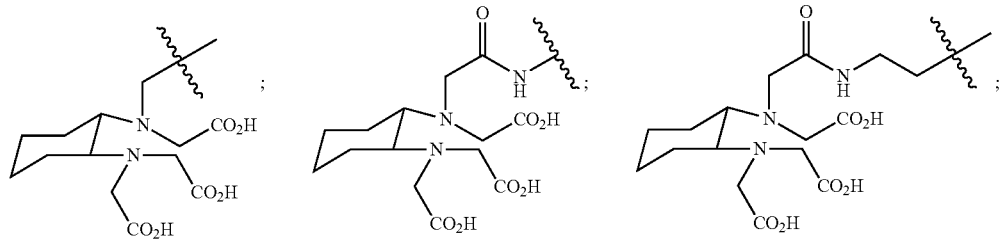
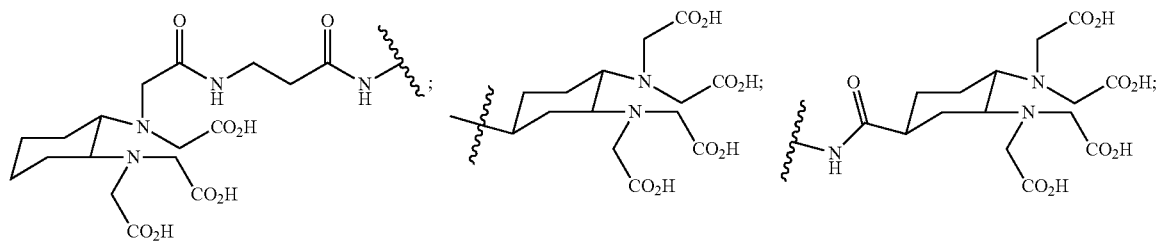
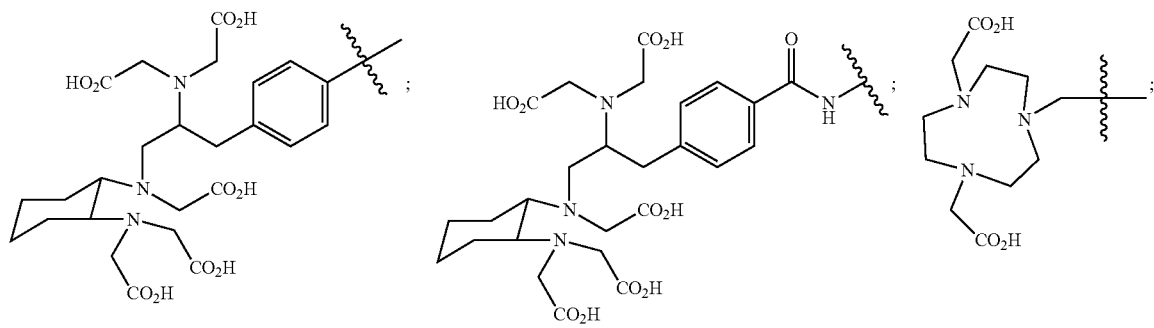
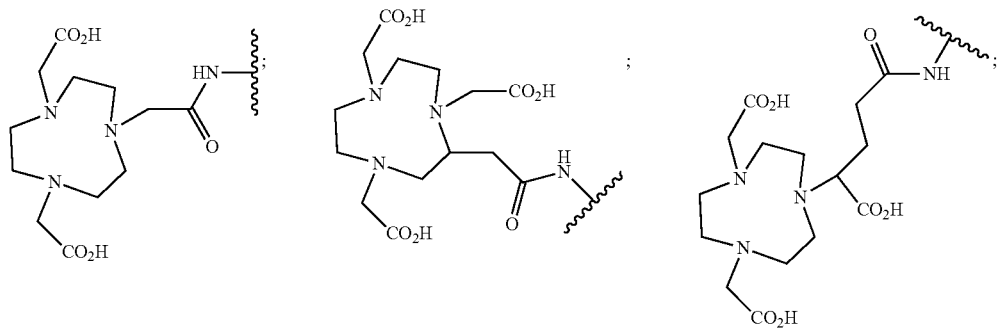

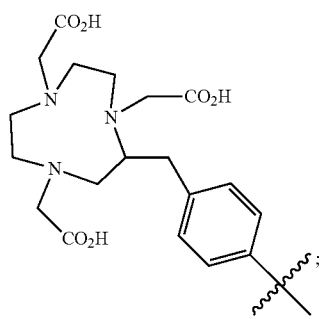
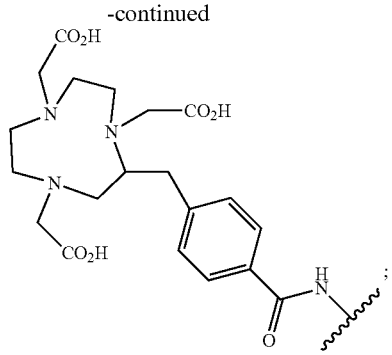
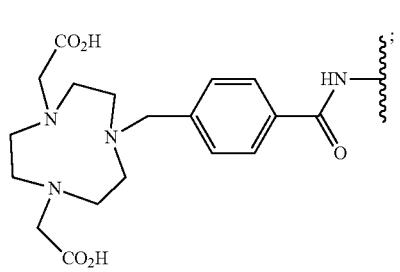
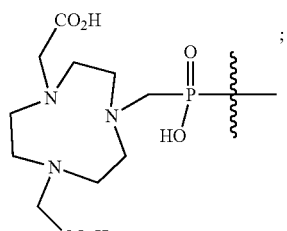
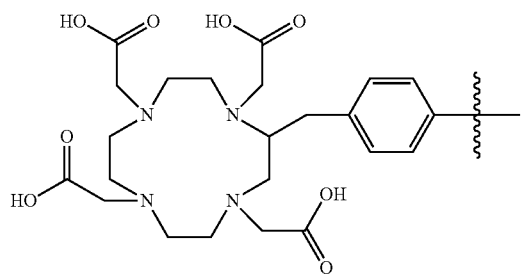
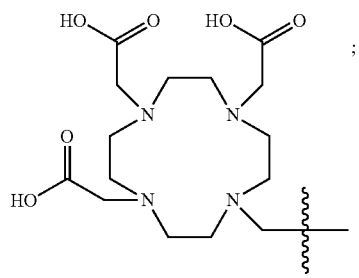
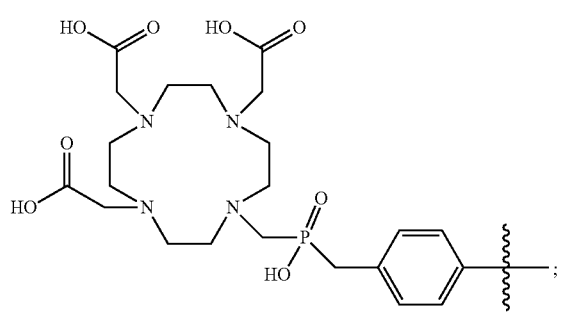
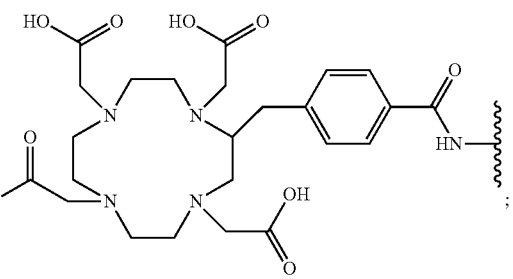
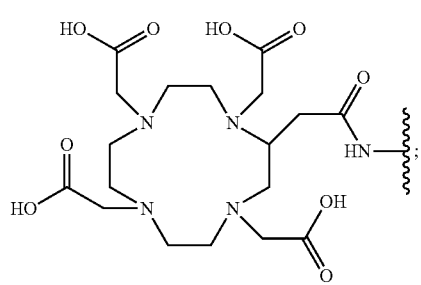
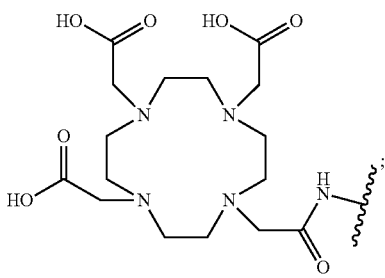

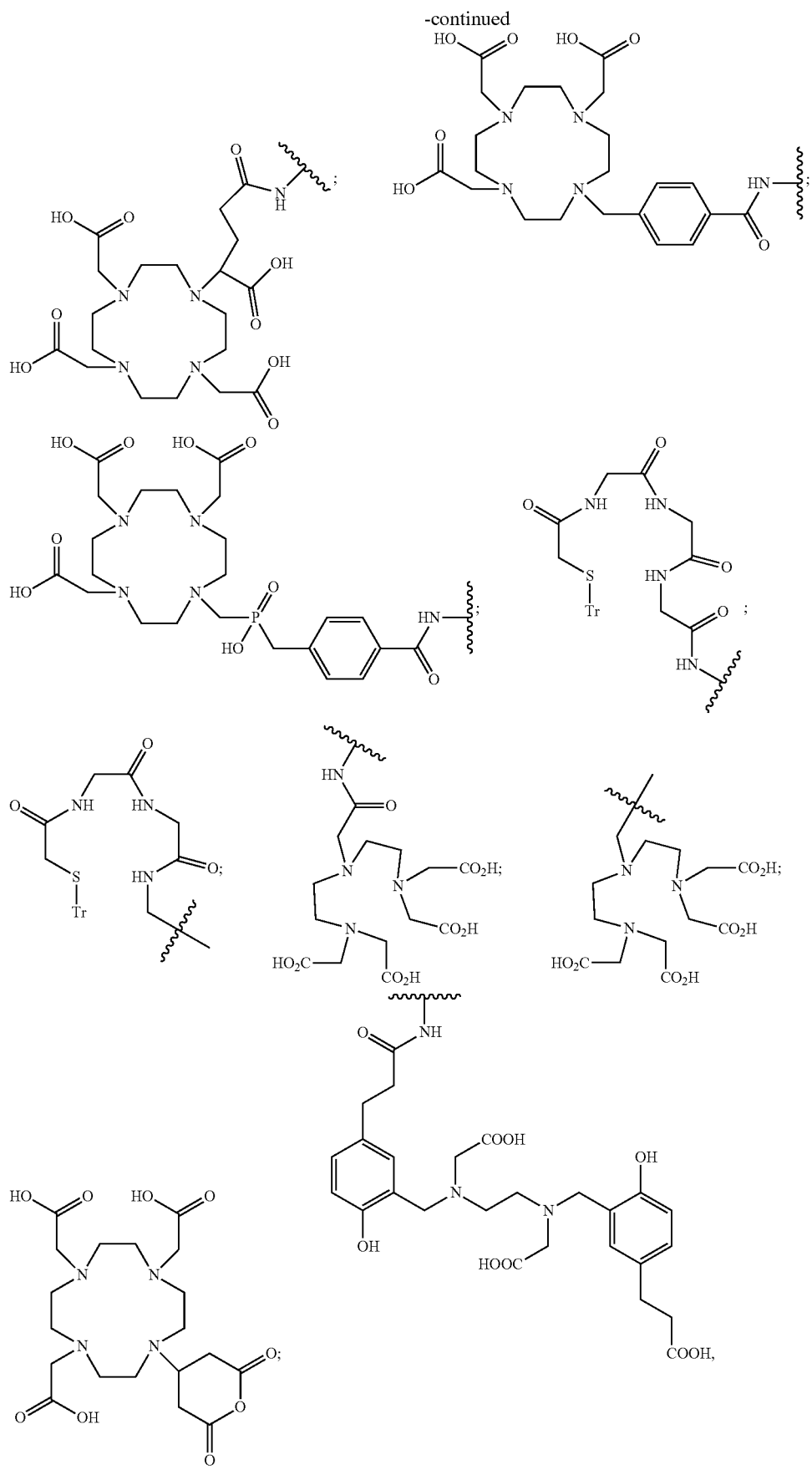

-continued

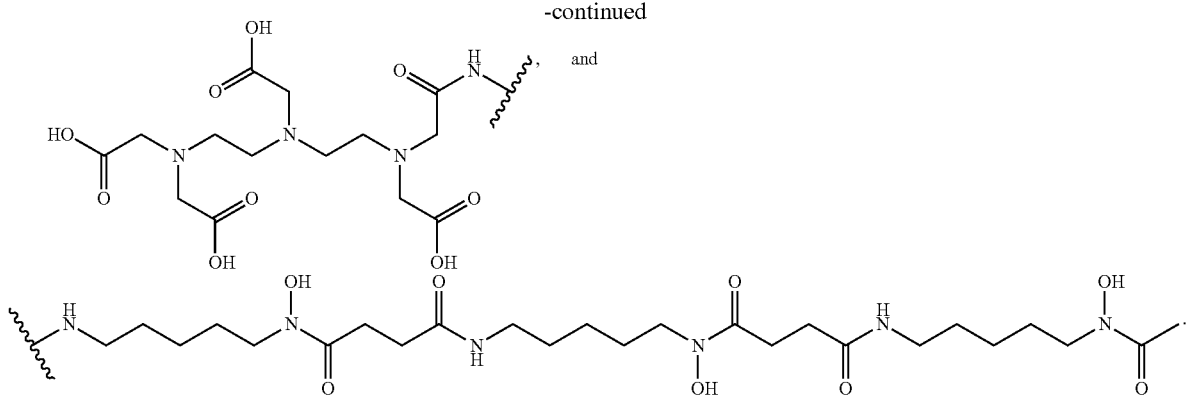

In some embodiments, B comprises an optical dye, e.g., in particular embodiments, a fluorescent dye. In some embodiments, the fluorescent dye moiety comprises carbocyanine, indocarbocyanine, oxacarbocyanine, thiacarbocyanine and merocyanine, polymethine, coumarine, rhodamine, xanthene, fluorescein, boron-dipyrromethane (BODIPY), Cy5, Cy5.5, Cy7, VivoTag-680, VivoTag-S680, VivoTag-S750, AlexaFluor660, AlexaFluor680, AlexaFluor700, AlexaFluor750, AlexaFluor790, Dy677, Dy676, Dy682, Dy752, Dy780, DyLight547, Dylight647, HiLyte Fluor 647, HiLyte Fluor 680, HiLyte Fluor 750, IRDye 800CW, IRDye 800RS, IRDye 700DX, ADS780WS, ADS830WS, and ADS832WS.

Representative optical dyes include, but are not limited to:

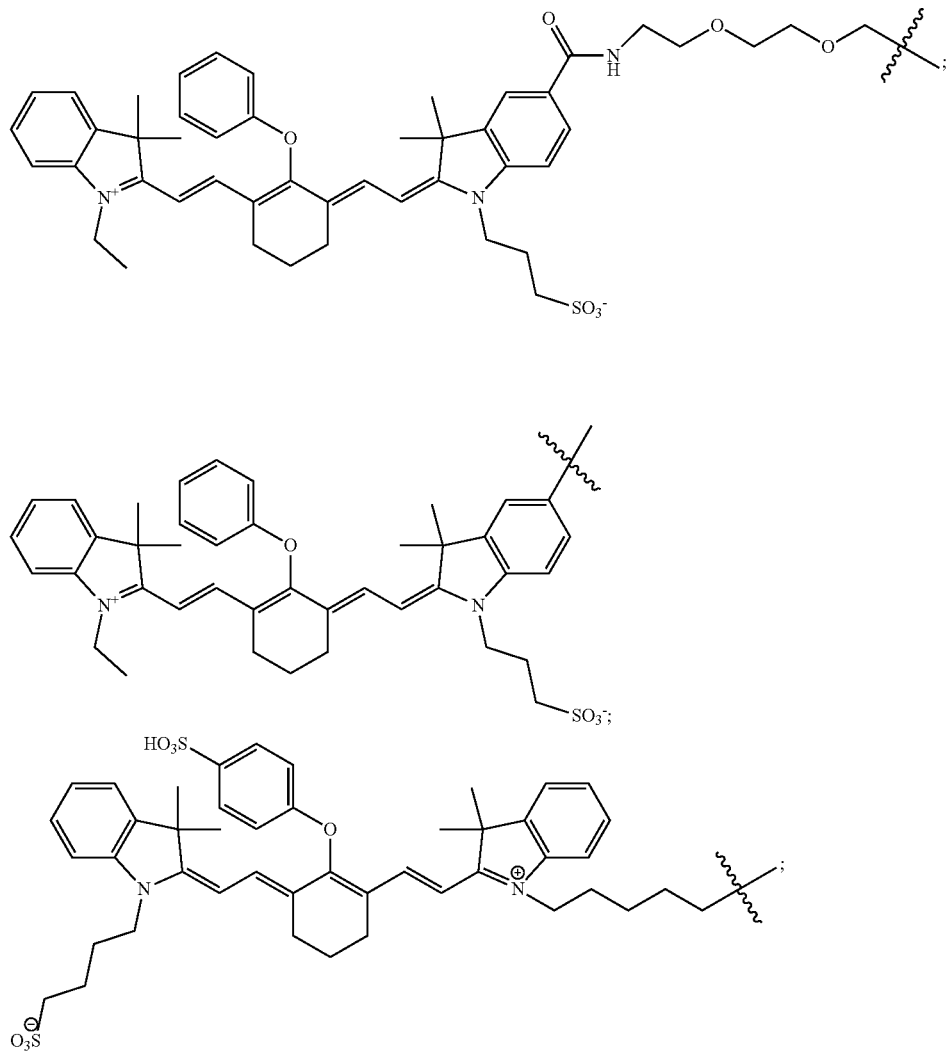

-continued
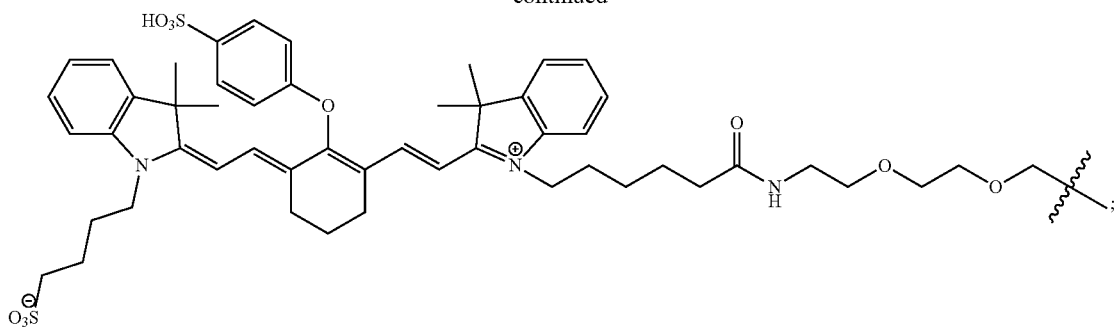
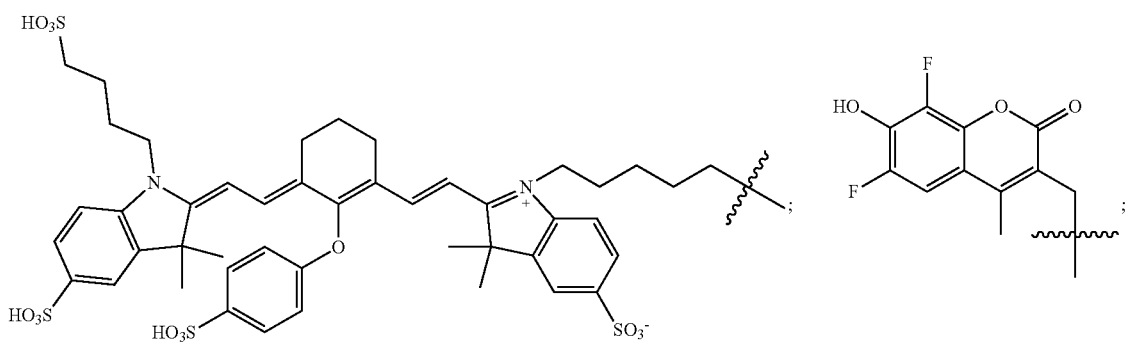
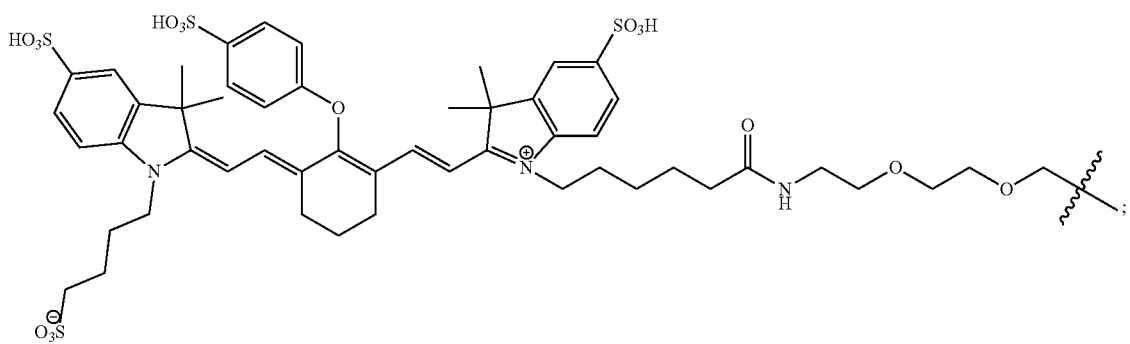
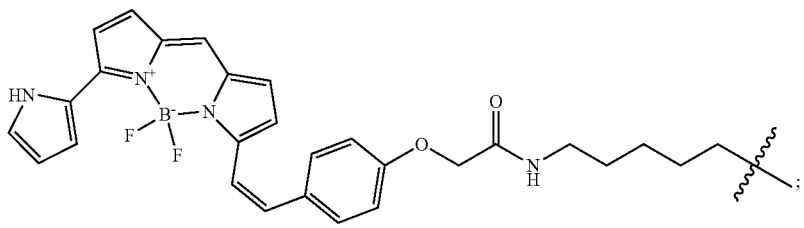
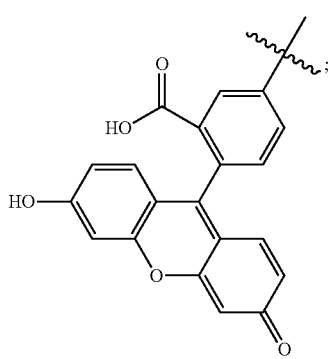

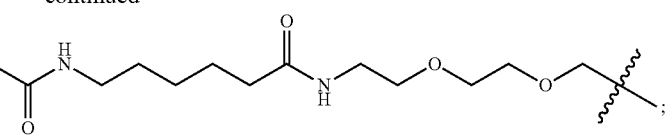
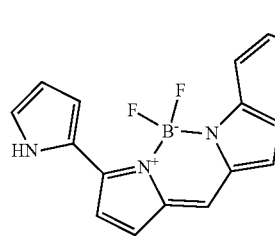
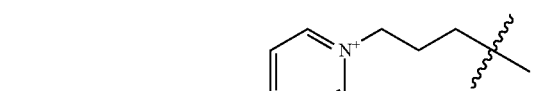
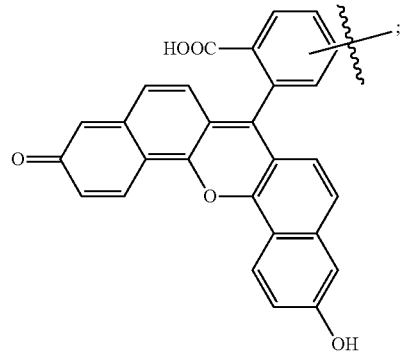
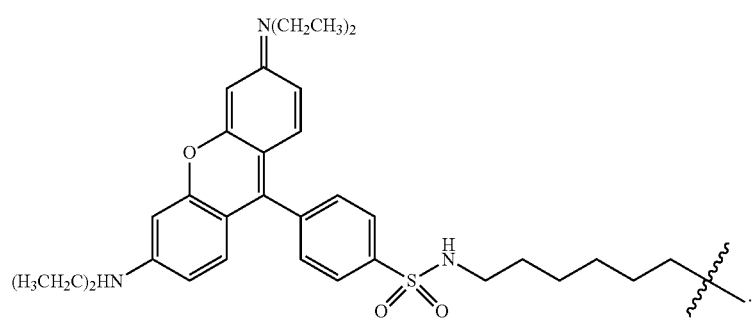
In some embodiments, the presently disclosed subject matter provides a compound selected from the group consisting of:
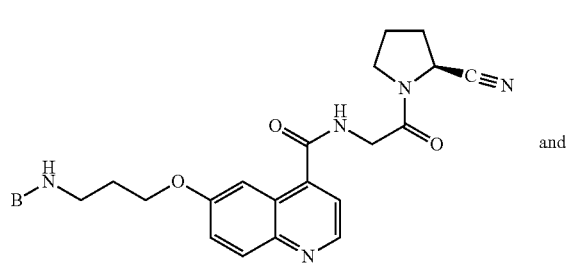
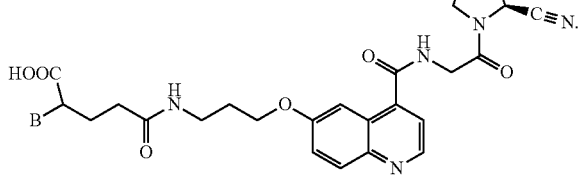
In particular embodiments, the compound is selected from the group consisting of:

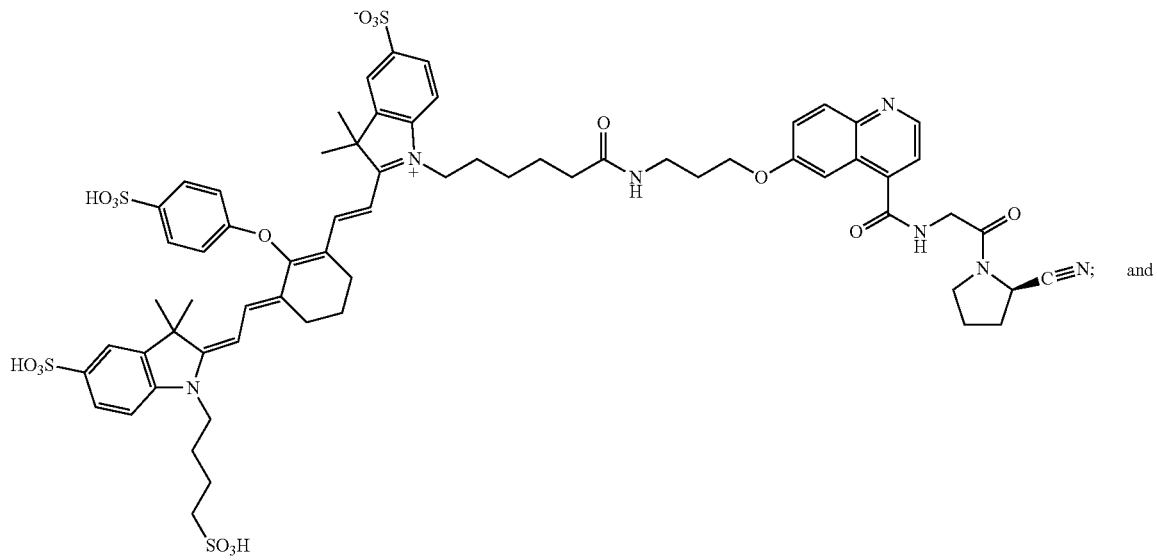

XY-FAP-01

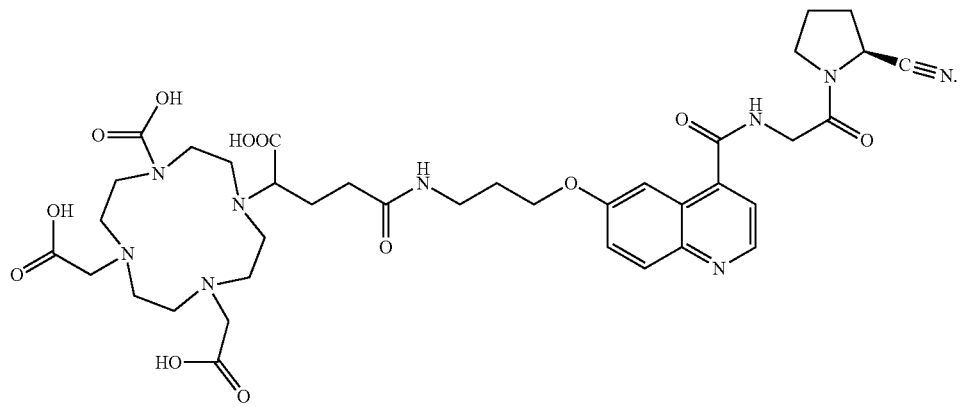

XY-FAP-02

B. Pharmaceutical Compositions and Administration

In another aspect, the present disclosure provides a pharmaceutical comprising a compound of formula (I) in admixture with a pharmaceutically acceptable carrier, diluent, excipient, or adjuvant. One of skill in the art will recognize that the pharmaceutical compositions include the pharmaceutically acceptable salts or hydrates of the compounds described above.

Pharmaceutically acceptable salts are generally well known to those of ordinary skill in the art and include salts of active compounds which are prepared with relatively nontoxic acids or bases, depending on the particular substituent moieties found on the compounds described herein. When compounds of the present disclosure contain relatively acidic functionalities, base addition salts can be obtained by contacting the neutral form of such compounds with a sufficient amount of the desired base, either neat or in a suitable inert solvent or by ion exchange, whereby one basic counterion (base) in an ionic complex is substituted for another. Examples of pharmaceutically acceptable base addition salts include sodium, potassium, calcium, ammonium, organic amino, or magnesium salt, or a similar salt.

When compounds of the present disclosure contain relatively basic functionalities, acid addition salts can be obtained by contacting the neutral form of such compounds with a sufficient amount of the desired acid, either neat or in a suitable inert solvent or by ion exchange, whereby one acidic counterion (acid) in an ionic complex is substituted for another. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-toluenesulfonic, citric, tartaric, methanesulfonic, and the like. Also included are salts of amino acids such as arginate and the like, and salts of organic acids like glucuronic or galactunoric acids and the like (see, for example, Berge et al, "Pharmaceutical Salts", Journal of Pharmaceutical Science, 1977, 66, 1-19). Certain specific compounds of the present disclosure contain both basic and acidic functionalities that allow the compounds to be converted into either base or acid addition salts.

Accordingly, pharmaceutically acceptable salts suitable for use with the presently disclosed subject matter include, by way of example but not limitation, acetate, benzenesulfonate, benzoate, bicarbonate, bitartrate, bromide, calcium edetate, carnsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington: The Science and Practice of Pharmacy ($20^{th}$ ed.) Lippincott, Williams & Wilkins (2000).

In therapeutic and/or diagnostic applications, the compounds of the disclosure can be formulated for a variety of modes of administration, including systemic and topical or localized administration. Techniques and formulations generally may be found in Remington: The Science and Practice of Pharmacy (20th ed.) Lippincott, Williams & Wilkins (2000).

Depending on the specific conditions being treated, such agents may be formulated into liquid or solid dosage forms and administered systemically or locally. The agents may be delivered, for example, in a timed- or sustained-slow release form as is known to those skilled in the art. Techniques for formulation and administration may be found in Remington: The Science and Practice of Pharmacy (20th ed.) Lippincott, Williams & Wilkins (2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articular, intra-sternal, intra-synovial, intra-hepatic, intralesional, intracranial, intraperitoneal, intranasal, or intraocular injections or other modes of delivery.

For injection, the agents of the disclosure may be formulated and diluted in aqueous solutions, such as in physiologically compatible buffers such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate the compounds herein disclosed for the practice of the disclosure into dosages suitable for systemic administration is within the scope of the disclosure. With proper choice of carrier and suitable manufacturing practice, the compositions of the present disclosure, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the disclosure to be formulated as tablets, pills, capsules, liquids, gels, syrups, slurries, suspensions and the like, for oral ingestion by a subject (e.g., patient) to be treated.

For nasal or inhalation delivery, the agents of the disclosure also may be formulated by methods known to those of skill in the art, and may include, for example, but not limited to, examples of solubilizing, diluting, or dispersing substances, such as saline; preservatives, such as benzyl alcohol; absorption promoters; and fluorocarbons.

Pharmaceutical compositions suitable for use in the present disclosure include compositions wherein the active ingredients are contained in an effective amount to achieve its intended purpose. Determination of the effective amounts is well within the capability of those skilled in the art, especially in light of the detailed disclosure provided herein. Generally, the compounds according to the disclosure are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. A non-limiting dosage is 10 to 30 mg per day. The exact dosage will depend upon the route of administration, the form in which the compound is administered, the subject to be treated, the body weight of the subject to be treated, the bioavailability of the compound(s), the adsorption, distribution, metabolism, and excretion (ADME) toxicity of the compound(s), and the preference and experience of the attending physician.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

C. Methods of Imaging Using the Compounds of Formula (I), or Pharmaceutical Compositions Thereof In some embodiments, presently disclosed subject matter provides a method for imaging a disease or disorder associated with fibroblast-activation protein-α (FAP-α), the method comprising administering a compound of formula (I), wherein the compound of formula (I) comprises an optical or radiolabeled functional group suitable for optical imaging, PET imaging, or SPECT imaging; and obtaining an image.

Accordingly, in some embodiments, the presently disclosed subject matter provides a method for imaging one or more cells, organs, or tissues, the method comprising exposing cells or administering to a subject an effective amount of a compound of formula (I) with an optical or radioisotopic label suitable for imaging. In some embodiments, the one or more organs or tissues include prostate tissue, kidney tissue, brain tissue, vascular tissue, or tumor tissue.

The imaging methods of the invention are suitable for imaging any physiological process or feature in which FAP-α is involved, for example, identifying areas of tissues or targets which exhibit or express high concentrations of FAP-α. Physiological processes in which FAP-α is involved include, but are not limited to: (a) proliferation diseases (including but not limited to cancer); (b) tissue remodeling and/or chronic inflammation (including but not limited to fibrotic disease, wound healing, keloid formation, osteoarthritis, rheumatoid arthritis and related disorders involving cartilage degradation); and (c) endocrinological disorders (including but not limited to disorders of glucose metabolism).

In certain embodiments, the radiolabeled compound is stable in vivo.

In certain embodiments, the radiolabeled compound is detected by positron emission tomography (PET) or single photon emission computed tomography (SPECT).

In certain embodiments, the optical reporting moiety is detected by fluorescence, such as fluorescence microscopy.

In certain embodiments, the presently disclosed compounds are excreted from tissues of the body quickly to prevent prolonged exposure to the radiation of the radiolabeled compound administered to the subject. Typically, the presently disclosed compounds are eliminated from the body in less than about 24 hours. More typically, the presently disclosed compounds are eliminated from the body in less than about 16 hours, 12 hours, 8 hours, 6 hours, 4 hours, 2 hours, 90 minutes, or 60 minutes. Exemplary compounds are eliminated in between about 60 minutes and about 120 minutes. In certain embodiments, the presently disclosed compounds are stable in vivo such that substantially all, e.g., more than about 50%, 60%, 70%, 80%, or 90% of the injected compound is not metabolized by the body prior to excretion.

Additionally, for in vitro applications, such as in vitro diagnostic and research applications, body fluids and cell samples of the above subjects will be suitable for use, such as mammalian, particularly primate such as human, blood, urine or tissue samples, or blood urine or tissue samples of the animals mentioned for veterinary applications.

Other embodiments provide kits comprising a compound of formula (I). In certain embodiments, the kit provides packaged pharmaceutical compositions comprising a pharmaceutically acceptable carrier and a compound of formula (I). In certain embodiments the packaged pharmaceutical composition will comprise the reaction precursors necessary to generate the compound of formula (I) upon combination with a radiolabeled precursor. Other packaged pharmaceutical compositions further comprise indicia comprising at least one of: instructions for preparing compounds of formula (I) from supplied precursors, instructions for using the composition to image cells or tissues expressing FAP-α.

In certain embodiments, a kit containing from about 1 to about 30 mCi of the radionuclide-labeled imaging agent described above, in combination with a pharmaceutically acceptable carrier, is provided. The imaging agent and carrier may be provided in solution or in lyophilized form. When the imaging agent and carrier of the kit are in lyophilized form, the kit may optionally contain a sterile and physiologically acceptable reconstitution medium such as water, saline, buffered saline, and the like. The kit may provide a compound of formula (I) in solution or in lyophilized form, and these components of the kit may optionally contain stabilizers such as NaCl, silicate, phosphate buffers, ascorbic acid, gentisic acid, and the like. Additional stabilization of kit components may be provided in this embodiment, for example, by providing the reducing agent in an oxidation-resistant form.

Determination and optimization of such stabilizers and stabilization methods are well within the level of skill in the art.

In certain embodiments, a kit provides a non-radiolabeled precursor to be combined with a radiolabeled reagent on-site.

Imaging agents may be used in accordance with the presently disclosed methods by one of skill in the art. Images can be generated by virtue of differences in the spatial distribution of the imaging agents which accumulate at a site when contacted with FAP-α. The spatial distribution may be measured using any means suitable for the particular label, for example, a gamma camera, a PET apparatus, a SPECT apparatus, and the like. The extent of accumulation of the imaging agent may be quantified using known methods for quantifying radioactive emissions or fluorescence. A particularly useful imaging approach employs more than one imaging agent to perform simultaneous studies.

In general, a detectably effective amount of the imaging agent of the invention is administered to a subject. A "detectably effective amount" of the imaging agent is defined as an amount sufficient to yield an acceptable image using equipment which is available for clinical use. A detectably effective amount of the imaging agent may be administered in more than one injection. The detectably effective amount of the imaging agent of the invention can vary according to factors such as the degree of susceptibility of the individual, the age, sex, and weight of the individual, idiosyncratic responses of the individual, and the dosimetry. Detectably effective amounts of the imaging agent also can vary according to instrument and film-related factors. Optimization of such factors is well within the level of skill in the art. The amount of imaging agent used for diagnostic purposes and the duration of the imaging study will depend upon the radionuclide used to label the agent, the body mass of the patient, the nature and severity of the condition being treated, the nature of therapeutic treatments which the patient has undergone, and on the idiosyncratic responses of the patient. Ultimately, the attending physician will decide the amount of imaging agent to administer to each individual patient and the duration of the imaging study.

D. Methods of Treating a FAP-α Related Disease or Disorder Using the Compounds of Formula (I), or Pharmaceutical Compositions Thereof In other embodiments, the presently disclosed compounds of formula (I) can be used to treat a subject afflicted with one or more FAP-α related diseases or disorders including, but not limited to: (a) proliferation (including but not limited to cancer); (b) tissue remodeling and/or chronic inflammation (including but not limited to fibrotic disease, wound healing, keloid formation, osteoarthritis, rheumatoid arthritis and related disorders involving cartilage degradation); and (c)

endocrinological disorders (including but not limited to disorders of glucose metabolism).

Accordingly, in some embodiments, the one or more FAP-α related disease or disorder is selected from the group consisting of a proliferative disease, including, but not limited to, breast cancer, colorectal cancer, ovarian cancer, prostate cancer, pancreatic cancer, kidney cancer, lung cancer, melanoma, fibrosarcoma, bone and connective tissue sarcomas, renal cell carcinoma, giant cell carcinoma, squamous cell carcinoma, and adenocarcinoma; diseases characterized by tissue remodeling and/or chronic inflammation; disorders involving endocrinological dysfunction; and blood clotting disorders.

In general, the "effective amount" of an active agent or drug delivery device refers to the amount necessary to elicit the desired biological response. As will be appreciated by those of ordinary skill in this art, the effective amount of an agent or device may vary depending on such factors as the desired biological endpoint, the agent to be delivered, the makeup of the pharmaceutical composition, the target tissue, and the like.

In other embodiments, the method can be practiced in vitro or ex vivo by introducing, and preferably mixing, the compound and cell(s) or tumor(s) in a controlled environment, such as a culture dish or tube. The method can be practiced in vivo, in which case contacting means exposing the target in a subject to at least one compound of the presently disclosed subject matter, such as administering the compound to a subject via any suitable route. According to the presently disclosed subject matter, contacting may comprise introducing, exposing, and the like, the compound at a site distant to the cells to be contacted, and allowing the bodily functions of the subject, or natural (e.g., diffusion) or man-induced (e.g., swirling) movements of fluids to result in contact of the compound and the target.

The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal (non-human) subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein. In some embodiments, the subject is human. In other embodiments, the subject is non-human.

As used herein, the term "treating" can include reversing, alleviating, inhibiting the progression of, preventing or reducing the likelihood of the disease, or condition to which such term applies, or one or more symptoms or manifestations of such disease or condition.

"Preventing" refers to causing a disease, condition, or symptom or manifestation of such, or worsening of the severity of such, not to occur. Accordingly, the presently disclosed compounds can be administered prophylactically to prevent or reduce the incidence or recurrence of the disease, or condition.

II. DEFINITIONS

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

While the following terms in relation to compounds of formula (I) are believed to be well understood by one of ordinary skill in the art, the following definitions are set forth to facilitate explanation of the presently disclosed subject matter. These definitions are intended to supplement and illustrate, not preclude, the definitions that would be apparent to one of ordinary skill in the art upon review of the present disclosure.

The terms substituted, whether preceded by the term "optionally" or not, and substituent, as used herein, refer to the ability, as appreciated by one skilled in this art, to change one functional group for another functional group on a molecule, provided that the valency of all atoms is maintained. When more than one position in any given structure may be substituted with more than one substituent selected from a specified group, the substituent may be either the same or different at every position. The substituents also may be further substituted (e.g., an aryl group substituent may have another substituent off it, such as another aryl group, which is further substituted at one or more positions).

Where substituent groups or linking groups are specified by their conventional chemical formulae, written from left to right, they equally encompass the chemically identical substituents that would result from writing the structure from right to left, e.g., —$CH_2O$— is equivalent to —$OCH_2$—; —$C(=O)O$— is equivalent to —$OC(=O)$—; —$OC(=O)NR$— is equivalent to —$NRC(=O)O$—, and the like.

When the term "independently selected" is used, the substituents being referred to (e.g., R groups, such as groups $R_1$, $R_2$, and the like, or variables, such as "m" and "n"), can be identical or different. For example, both $R_1$ and $R_2$ can be substituted alkyls, or $R_1$ can be hydrogen and $R_2$ can be a substituted alkyl, and the like.

The terms "a," "an," or "a(n)," when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

A named "R" or group will generally have the structure that is recognized in the art as corresponding to a group having that name, unless specified otherwise herein. For the purposes of illustration, certain representative "R" groups as set forth above are defined below.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

Unless otherwise explicitly defined, a "substituent group," as used herein, includes a functional group selected from one or more of the following moieties, which are defined herein:

The term hydrocarbon, as used herein, refers to any chemical group comprising hydrogen and carbon. The hydrocarbon may be substituted or unsubstituted. As would be known to one skilled in this art, all valencies must be satisfied in making any substitutions. The hydrocarbon may be unsaturated, saturated, branched, unbranched, cyclic, polycyclic, or heterocyclic. Illustrative hydrocarbons are further defined herein below and include, for example, methyl, ethyl, n-propyl, isopropyl, cyclopropyl, allyl, vinyl, n-butyl, tert-butyl, ethynyl, cyclohexyl, and the like.

The term "alkyl," by itself or as part of another substituent, means, unless otherwise stated, a straight (i.e., unbranched) or branched chain, acyclic or cyclic hydrocarbon group, or combination thereof, which may be fully saturated, mono- or polyunsaturated and can include di- and multivalent groups, having the number of carbon atoms designated (i.e., $C_1$-$C_{10}$ means one to ten carbons, including 1, 2, 3, 4, 5, 6, 7, 8, 9, and 10 carbons). In particular embodiments, the term "alkyl" refers to $C_{1-20}$ inclusive, including 1, 2, 3, 4, 5, 6, 7, 8, 9, 10, 11, 12, 13, 14, 15, 16, 17, 18, 19, and 20 carbons, linear (i.e., "straight-chain"), branched, or cyclic, saturated or at least partially and in some cases fully unsaturated (i.e., alkenyl and alkynyl) hydrocarbon radicals derived from a hydrocarbon moiety containing between one and twenty carbon atoms by removal of a single hydrogen atom.

Representative saturated hydrocarbon groups include, but are not limited to, methyl, ethyl, n-propyl, isopropyl, n-butyl, isobutyl, sec-butyl, tert-butyl, n-pentyl, sec-pentyl, isopentyl, neopentyl, n-hexyl, sec-hexyl, n-heptyl, n-octyl, n-decyl, n-undecyl, dodecyl, cyclohexyl, (cyclohexyl)methyl, cyclopropylmethyl, and homologs and isomers thereof.

"Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, alkylamino, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "heteroalkyl," by itself or in combination with another term, means, unless otherwise stated, a stable straight or branched chain, or cyclic hydrocarbon group, or combinations thereof, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$S—S(O)—$CH_3$, —$CH_2$—$CH_2$—S(O)$_2$—$CH_3$, —CH=CH—O—$CH_3$, —Si($CH_3$)$_3$, —$CH_2$—CH=N—O$CH_3$, —CH=CH—N($CH_3$)—$CH_3$, O—$CH_3$, —O—$CH_2$—$CH_3$, and —CN. Up to two or three heteroatoms may be consecutive, such as, for example, —$CH_2$—NH—O$CH_3$ and —$CH_2$—O—Si($CH_3$)$_3$.

As described above, heteroalkyl groups, as used herein, include those groups that are attached to the remainder of the molecule through a heteroatom, such as —C(O)NR', —NR'R", —OR', —SR, —S(O)R, and/or —S(O$_2$)R'. Where "heteroalkyl" is recited, followed by recitations of specific heteroalkyl groups, such as —NR'R or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, unsubstituted alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl, and fused ring systems, such as dihydro- and tetrahydronaphthalene, and the like.

The term "cycloalkylalkyl," as used herein, refers to a cycloalkyl group as defined hereinabove, which is attached to the parent molecular moiety through an alkyl group, also as defined above. Examples of cycloalkylalkyl groups include cyclopropylmethyl and cyclopentylethyl.

The terms "cycloheteroalkyl" or "heterocycloalkyl" refer to a non-aromatic ring system, unsaturated or partially unsaturated ring system, such as a 3- to 10-member substituted or unsubstituted cycloalkyl ring system, including one or more heteroatoms, which can be the same or different, and are selected from the group consisting of nitrogen (N), oxygen (O), sulfur (S), phosphorus (P), and silicon (Si), and optionally can include one or more double bonds.

The cycloheteroalkyl ring can be optionally fused to or otherwise attached to other cycloheteroalkyl rings and/or non-aromatic hydrocarbon rings. Heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocylic refers to a non-aromatic 5-, 6-, or 7-membered ring or a polycyclic group wherein at least one ring atom is a heteroatom selected from O, S, and N (wherein the nitrogen and sulfur heteroatoms may be optionally oxidized), including, but not limited to, a bi- or tri-cyclic group, comprising fused six-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Representative cycloheteroalkyl ring systems include, but are not limited to pyrrolidinyl, pyrrolinyl, imidazolidinyl, imidazolinyl, pyrazolidinyl, pyrazolinyl, piperidyl, piperazinyl, indolinyl, quinuclidinyl, morpholinyl, thiomorpholinyl, thiadiazinanyl, tetrahydrofuranyl, and the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. Alkyl groups which are limited to hydrocarbon groups are termed "homoalkyl."

More particularly, the term "alkenyl" as used herein refers to a monovalent group derived from a $C_{1-20}$ inclusive straight or branched hydrocarbon moiety having at least one carbon-carbon double bond by the removal of a single hydrogen molecule. Alkenyl groups include, for example, ethenyl (i.e., vinyl), propenyl, butenyl, 1-methyl-2-buten-1-yl, pentenyl, hexenyl, octenyl, allenyl, and butadienyl.

The term "cycloalkenyl" as used herein refers to a cyclic hydrocarbon containing at least one carbon-carbon double bond. Examples of cycloalkenyl groups include cyclopropenyl, cyclobutenyl, cyclopentenyl, cyclopentadienyl, cyclohexenyl, 1,3-cyclohexadienyl, cycloheptenyl, cycloheptatrienyl, and cyclooctenyl.

The term "alkynyl" as used herein refers to a monovalent group derived from a straight or branched $C_{1-20}$ hydrocarbon of a designed number of carbon atoms containing at least one carbon-carbon triple bond. Examples of "alkynyl" include ethynyl, 2-propynyl (propargyl), 1-propynyl, pentynyl, hexynyl, and heptynyl groups, and the like.

The term "alkylene" by itself or a part of another substituent refers to a straight or branched bivalent aliphatic hydrocarbon group derived from an alkyl group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—$CH_2$—); ethylene (—$CH_2$—$CH_2$—); propylene (—$(CH_2)_3$—); cyclohexylene (—$C_6H_{10}$—); CH═CH—CH═CH—; —CH═CH—$CH_2$—; —$CH_2CH_2CH_2CH_2$—, —$CH_2$CH═CH$CH_2$—, —$CH_2$CsC$CH_2$—, —$CH_2CH_2$CH($CH_2CH_2CH_3$)$CH_2$—, —$(CH_2)_q$—N(R)—$(CH_2)_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—$CH_2$—O—); and ethylenedioxyl (—O—$(CH_2)_2$—O—). An alkylene group can have about 2 to about 3 carbon atoms and can further have 6-20 carbons. Typically, an alkyl (or alkylene) group will have from 1 to 24 carbon atoms, with those groups having 10 or fewer carbon atoms being some embodiments of the present disclosure. A "lower alkyl" or "lower alkylene" is a shorter chain alkyl or alkylene group, generally having eight or fewer carbon atoms.

The term "heteroalkylene" by itself or as part of another substituent means a divalent group derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms also can occupy either or both of the chain termini (e.g., alkyleneoxo, alkylenedioxo, alkylencamino, alkylenediamino, and the like). Still further, for alkylene and heteroalkylene linking groups, no orientation of the linking group is implied by the direction in which the formula of the linking group is written. For example, the formula —C(O)OR'-represents both-C(O)OR'— and —R'OC(O)—.

The term "aryl" means, unless otherwise stated, an aromatic hydrocarbon substituent that can be a single ring or multiple rings (such as from 1 to 3 rings), which are fused together or linked covalently. The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent forms of aryl and heteroaryl, respectively.

For brevity, the term "aryl" when used in combination with other terms (e.g., aryloxy, arylthioxy, arylalkyl) includes both aryl and heteroaryl rings as defined above. Thus, the terms "arylalkyl" and "heteroarylalkyl" are meant to include those groups in which an aryl or heteroaryl group is attached to an alkyl group (e.g., benzyl, phenethyl, pyridylmethyl, furylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). However, the term "haloaryl," as used herein is meant to cover only aryls substituted with one or more halogens.

Where a heteroalkyl, heterocycloalkyl, or heteroaryl includes a specific number of members (e.g. "3 to 7 membered"), the term "member" refers to a carbon or heteroatom.

Further, a structure represented generally by the formula:

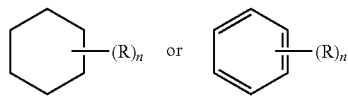

as used herein refers to a ring structure, for example, but not limited to a 3-carbon, a 4-carbon, a 5-carbon, a 6-carbon, a 7-carbon, and the like, aliphatic and/or aromatic cyclic compound, including a saturated ring structure, a partially saturated ring structure, and an unsaturated ring structure, comprising a substituent R group, wherein the R group can be present or absent, and when present, one or more R groups can each be substituted on one or more available carbon atoms of the ring structure. The presence or absence of the R group and number of R groups is determined by the value of the variable "n," which is an integer generally having a value ranging from 0 to the number of carbon atoms on the ring available for substitution. Each R group, if more than one, is substituted on an available carbon of the ring structure rather than on another R group. For example, the structure above where n is 0 to 2 would comprise compound groups including, but not limited to:

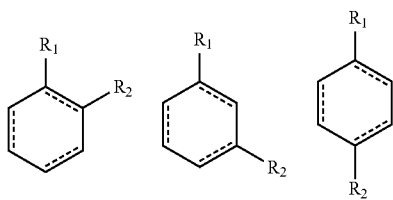

and the like.

A dashed line representing a bond in a cyclic ring structure indicates that the bond can be either present or absent in the ring. That is, a dashed line representing a bond in a cyclic ring structure indicates that the ring structure is selected from the group consisting of a saturated ring structure, a partially saturated ring structure, and an unsaturated ring structure.

The symbol ( $\sim\!\sim\!\sim\!\sim$ ) denotes the point of attachment of a moiety to the remainder of the molecule.

When a named atom of an aromatic ring or a heterocyclic aromatic ring is defined as being "absent," the named atom is replaced by a direct bond.

Each of above terms (e.g., "alkyl," "heteroalkyl," "cycloalkyl, and "heterocycloalkyl", "aryl," "heteroaryl," "phosphonate," and "sulfonate" as well as their divalent derivatives) are meant to include both substituted and unsubstituted forms of the indicated group. Optional substituents for each type of group are provided below.

Substituents for alkyl, heteroalkyl, cycloalkyl, heterocycloalkyl monovalent and divalent derivative groups (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', —O, =NR', =N—OR', —NR'R", —SR', -halogen, —SiR'R"R'", —OC(O)R', —C(O)R', —CO$_2$R', —C(O)NR'R", —OC(O)NR'R", —NR"C(O)R', —NR'—C(O)NR"R'", —NR"C(O)OR', —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such groups. R', R", R'" and R'"' each may independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. As used herein, an "alkoxy" group is an alkyl attached to the remainder of the molecule through a divalent oxygen. When a compound of the disclosure includes more than one R group, for example, each of the R groups is independently selected as are each R', R", R'" and R'"' groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for alkyl groups above, exemplary substituents for aryl and heteroaryl groups (as well as their divalent derivatives) are varied and are selected from, for example: halogen, —OR', —NR'R", —SR', —SiR'R"R'", —OC(O)R', —C(O)R', —CO$_2$R', —C(O)NR'R", —OC(O)NR'R", —NR"C(O)R', —NR'—C(O)NR"R'"', —NR"C(O)OR', —NR—C(NR'R"R'") =NR'"', —NR—C(NR'R")=NR'"-S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxo, and fluoro(C$_1$-C$_4$)alkyl, in a number ranging from zero to the total number of open valences on aromatic ring system; and where R', R", R'" and R'"' may be independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R group, for example, each of the R groups is independently selected as are each R', R", R'" and R'"' groups when more than one of these groups is present.

Two of the substituents on adjacent atoms of aryl or heteroaryl ring may optionally form a ring of the formula —T—C(O)—(CRR')$_q$—U—, wherein T and U are independently —NR—, —O—, —CRR'- or a single bond, and q is an integer of from 0 to 3. Alternatively, two of the substituents on adjacent atoms of aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'- or a single bond, and r is an integer of from 1 to 4.

One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'—(C"R'")$_d$—, where s and d are independently integers of from 0 to 3, and X' is —O—, —NR'—, —S—, —S(O)—, —S(O)$_2$—, or —S(O)$_2$NR'—. The substituents R, R', R" and R'" may be independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "acyl" refers to an organic acid group wherein the —OH of the carboxyl group has been replaced with another substituent and has the general formula RC(=O)—, wherein R is an alkyl, alkenyl, alkynyl, aryl, carbocyclic, heterocyclic, or aromatic heterocyclic group as defined herein). As such, the term "acyl" specifically includes arylacyl groups, such as a 2-(furan-2-yl) acetyl)- and a 2-phenylacetyl group. Specific examples of acyl groups include acetyl and benzoyl. Acyl groups also are intended to include amides, —RC(=O)NR', esters, —RC(=O)OR', ketones, —RC(=O)R', and aldehydes, —RC(=O)H.

The terms "alkoxyl" or "alkoxy" are used interchangeably herein and refer to a saturated (i.e., alkyl-O—) or unsaturated (i.e., alkenyl-O— and alkynyl-O—) group attached to the parent molecular moiety through an oxygen atom, wherein the terms "alkyl," "alkenyl," and "alkynyl" are as previously described and can include C$_{1-20}$ inclusive, linear, branched, or cyclic, saturated or unsaturated oxo-hydrocarbon chains, including, for example, methoxyl, ethoxyl, propoxyl, isopropoxyl, n-butoxyl, sec-butoxyl, tert-butoxyl, and n-pentoxyl, neopentoxyl, n-hexoxyl, and the like.

The term "alkoxyalkyl" as used herein refers to an alkyl-O-alkyl ether, for example, a methoxyethyl or an ethoxymethyl group.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl-group wherein aryl and alkyl are as previously described and includes substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl, i.e., C$_6$H$_5$—CH$_2$—O—. An aralkyloxyl group can optionally be substituted.

"Alkoxycarbonyl" refers to an alkyl-O—C(=O)— group. Exemplary alkoxycarbonyl groups include methoxycarbonyl, ethoxycarbonyl, butyloxycarbonyl, and tert-butyloxycarbonyl.

"Aryloxycarbonyl" refers to an aryl-O—C(=O)— group. Exemplary aryloxycarbonyl groups include phenoxy- and naphthoxy-carbonyl.

"Aralkoxycarbonyl" refers to an aralkyl-O—C(=O)— group. An exemplary aralkoxycarbonyl group is benzyloxycarbonyl.

"Carbamoyl" refers to an amide group of the formula —C(=O)NH$_2$. "Alkylcarbamoyl" refers to a R'RN—C(=O)— group wherein one of R and R' is hydrogen and the other of R and R' is alkyl and/or substituted alkyl as previously described. "Dialkylcarbamoyl" refers to a R'RN—C(=O)— group wherein each of R and R' is independently alkyl and/or substituted alkyl as previously described.

The term carbonyldioxyl, as used herein, refers to a carbonate group of the formula —O—C(=O)—OR.

"Acyloxyl" refers to an acyl-O— group wherein acyl is as previously described. The term "amino" refers to the —NH$_2$ group and also refers to a nitrogen containing group as is known in the art derived from ammonia by the replacement of one or more hydrogen radicals by organic radicals. For example, the terms "acylamino" and "alkylamino" refer to specific N-substituted organic radicals with acyl and alkyl substituent groups respectively.

An "aminoalkyl" as used herein refers to an amino group covalently bound to an alkylene linker. More particularly, the terms alkylamino, dialkylamino, and trialkylamino as used herein refer to one, two, or three, respectively, alkyl groups, as previously defined, attached to the parent molecular moiety through a nitrogen atom. The term alkylamino refers to a group having the structure-NHR' wherein R' is an alkyl group, as previously defined; whereas the term dialkylamino refers to a group having the structure-NR'R", wherein R' and R" are each independently selected from the group consisting of alkyl groups. The term trialkylamino refers to a group having the structure-NR'R"R'", wherein R', R", and R'" are each independently selected from the group consisting of alkyl groups. Additionally, R', R", and/or R'" taken together may optionally be —(CH$_2$)$_k$— where k is an integer from 2 to 6. Examples include, but are not limited to, methylamino, dimethylamino, ethylamino, diethylamino, diethylaminocarbonyl, methylethylamino, isopropylamino, piperidino, trimethylamino, and propylamino.

The amino group is —NR'R", wherein R' and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

The terms alkylthioether and thioalkoxyl refer to a saturated (i.e., alkyl-S—) or unsaturated (i.e., alkenyl-S— and alkynyl-S—) group attached to the parent molecular moiety through a sulfur atom. Examples of thioalkoxyl moieties include, but are not limited to, methylthio, ethylthio, propylthio, isopropylthio, n-butylthio, and the like.

"Acylamino" refers to an acyl-NH— group wherein acyl is as previously described. "Aroylamino" refers to an aroyl-NH— group wherein aroyl is as previously described.

The term "carbonyl" refers to the —C(=O)— group, and can include an aldehyde group represented by the general formula R—C(=O)H.

The term "carboxyl" refers to the —COOH group. Such groups also are referred to herein as a "carboxylic acid" moiety.

The terms "halo," "halide," or "halogen" as used herein refer to fluoro, chloro, bromo, and iodo groups. Additionally, terms such as "haloalkyl," are meant to include monohaloalkyl and polyhaloalkyl. For example, the term "halo(C$_1$-

$C_4$)alkyl" is mean to include, but not be limited to, trifluoromethyl, 2,2,2-trifluoroethyl, 4-chlorobutyl, 3-bromopropyl, and the like.

The term "hydroxyl" refers to the —OH group.

The term "hydroxyalkyl" refers to an alkyl group substituted with an —OH group.

The term "mercapto" refers to the —SH group.

The term "oxo" as used herein means an oxygen atom that is double bonded to a carbon atom or to another element.

The term "nitro" refers to the —$NO_2$ group.

The term "thio" refers to a compound described previously herein wherein a carbon or oxygen atom is replaced by a sulfur atom.

The term "sulfate" refers to the —$SO_4$ group.

The term thiohydroxyl or thiol, as used herein, refers to a group of the formula —SH.

More particularly, the term "sulfide" refers to compound having a group of the formula —SR.

The term "sulfone" refers to compound having a sulfonyl group-$S(O_2)R$.

The term "sulfoxide" refers to a compound having a sulfinyl group-S(O)R

The term ureido refers to a urea group of the formula —NH—CO—$NH_2$.

Throughout the specification and claims, a given chemical formula or name shall encompass all tautomers, congeners, and optical- and stereoisomers, as well as racemic mixtures where such isomers and mixtures exist.

Certain compounds of the present disclosure may possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as D- or L- for amino acids, and individual isomers are encompassed within the scope of the present disclosure. The compounds of the present disclosure do not include those which are known in art to be too unstable to synthesize and/or isolate. The present disclosure is meant to include compounds in racemic, scalemic, and optically pure forms. Optically active (R)- and (S)-, or D- and L-isomers may be prepared using chiral synthons or chiral reagents, or resolved using conventional techniques. When the compounds described herein contain olefenic bonds or other centers of geometric asymmetry, and unless specified otherwise, it is intended that the compounds include both E and Z geometric isomers.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

It will be apparent to one skilled in the art that certain compounds of this disclosure may exist in tautomeric forms, all such tautomeric forms of the compounds being within the scope of the disclosure. The term "tautomer," as used herein, refers to one of two or more structural isomers which exist in equilibrium and which are readily converted from one isomeric form to another.

As used herein the term "monomer" refers to a molecule that can undergo polymerization, thereby contributing constitutional units to the essential structure of a macromolecule or polymer.

A "polymer" is a molecule of high relative molecule mass, the structure of which essentially comprises the multiple repetition of unit derived from molecules of low relative molecular mass, i.e., a monomer.

A "dendrimer" is highly branched, star-shaped macromolecules with nanometer-scale dimensions.

As used herein, an "oligomer" includes a few monomer units, for example, in contrast to a polymer that potentially can comprise an unlimited number of monomers. Dimers, trimers, and tetramers are non-limiting examples of oligomers.

The term "protecting group" refers to chemical moieties that block some or all reactive moieties of a compound and prevent such moieties from participating in chemical reactions until the protective group is removed, for example, those moieties listed and described in T. W. Greene, P. G. M. Wuts, Protective Groups in Organic Synthesis, 3rd ed. John Wiley & Sons (1999). It may be advantageous, where different protecting groups are employed, that each (different) protective group be removable by a different means. Protective groups that are cleaved under totally disparate reaction conditions allow differential removal of such protecting groups. For example, protective groups can be removed by acid, base, and hydrogenolysis. Groups such as trityl, dimethoxytrityl, acetal and tert-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, without limitation, methyl, ethyl, and acetyl in the presence of amines blocked with acid labile groups such as tert-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be blocked with oxidatively-removable protective groups such as 2,4-dimethoxybenzyl, while co-existing amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a palladium(O)— catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typical blocking/protecting groups include, but are not limited to the following moieties:

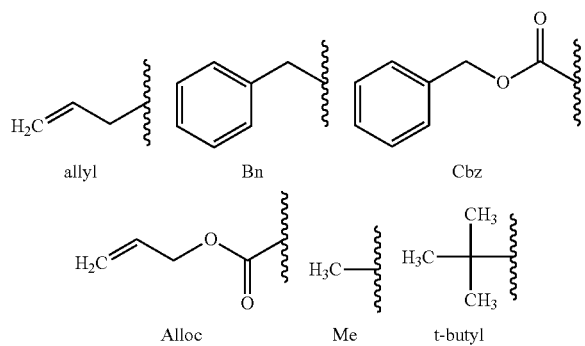

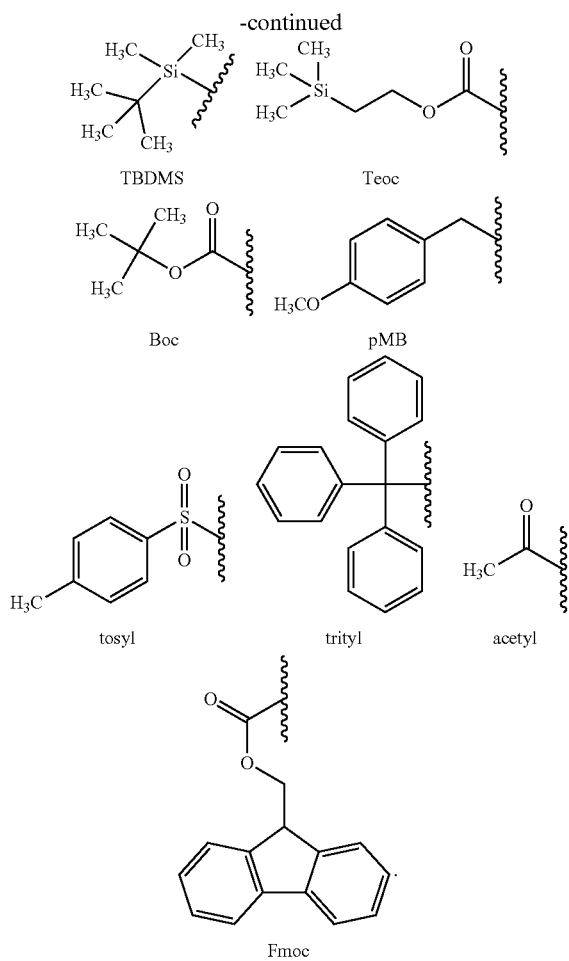

TBDMS  Teoc

Boc  pMB tosyl  trityl  acetyl

Fmoc

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, +100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Experimental Procedures 1.1 Synthesis of XY-FAP-01

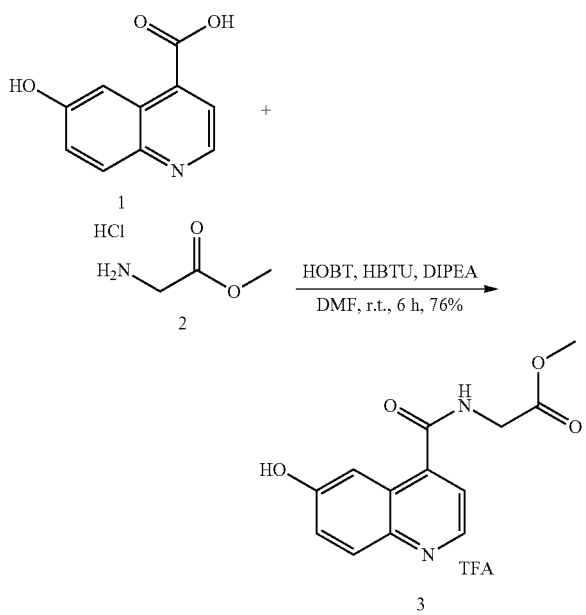

Methyl (6-hydroxyquinoline-4-carbonyl)glycinate (3): 6-Hydroxyquinoline-4-carboxylic acid (1) 210 mg (1.1 mmol), methyl glycinate HCl salt (2) 143 mg (1.1 mmol), HBTU 420 mg (1.1 mmol) and HOBt 170 mg (1.1 mmol) were dissolved in 12 mL dry DMF. To the solution, 0.77 mL of DIPEA (4.4 mmol) was added. The reaction was stirred at room temperature for 6 h. After the solvent was removed under vacuum, the mixture was loaded onto a 25 g C18 cartridge (Silicycle, Canada) and the product was purified with a MeCN/water/TFA gradient (0/100/0.1 to 90/10/0.1). 290 mg of product 3 was obtained as a yellow powder with a yield of 76%. 1H-NMR (400 MHz, CD$_3$OD): δ 8.69 (s, 1H), 7.94 (d, J=7.92 Hz, 1H), 7.57-7.51 (m, 3H), 7.42-7.37 (m, 1H), 4.21 (s, 2H), 3.81 (s, 3H). $^{13}$C-NMR (100 MHZ, CD$_3$OD): δ 172.4, 160.9, 145.1, 143.7, 129.7, 129.4, 128.3, 121.8, 119.6, 112.4, 109.1, 56.8, 44.8. MS: calculated for [C$_{13}$H$_{13}$N$_2$O$_4$]$^+$, 261.3 [M+H]$^+$; found 261.1.

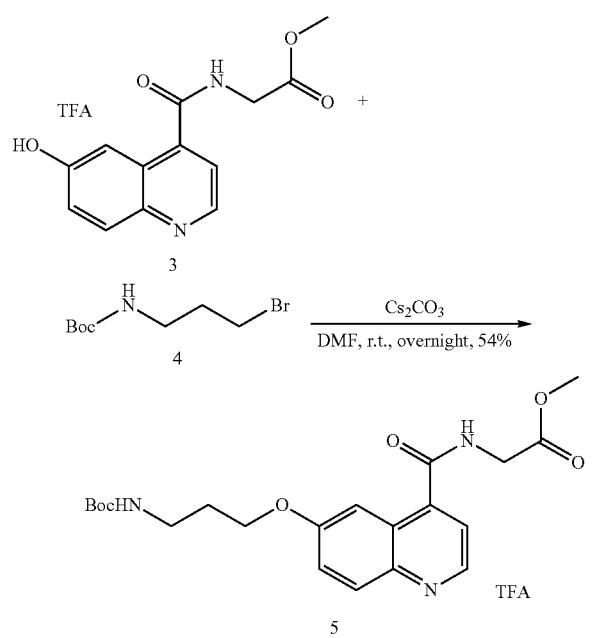

Methyl (6-(3-((tert-butoxycarbonyl)amino)propoxy)quinoline-4-carbonyl)glycinate (5): Methyl (6-hydroxyquinoline-4-carbonyl)glycinate (3) 360 mg (1.0 mmol), tert-butyl (3-bromopropyl)carbamate (4) 500 mg (2.1 mmol) were dissolved in 20 mL DMF. Cs$_2$CO$_3$ 1 g (3.0 mmol) was added to the solution and the reaction was stirred at room temperature overnight. After filtration, the solvent was removed under vacuum and the remaining mixture was loaded onto a 25 g C18 cartridge (Silicycle, Canada). The product was purified with a MeCN/water/TFA gradient (0/100/0.1 to 90/10/0.1). 270 mg of product 5 was obtained with a yield of 54%. 1H-NMR (400 MHZ, CDCl$_3$): δ 8.68-8.37 (m, 2H), 8.02 (d, J=9.1 Hz, 1H), 7.80 (s, 1H), 7.72-7.64 (m, 1H), 7.40 (d, J=9.1 Hz, 1H), 4.94 (br s, 1H), 4.41-4.31 (m, 2H), 4.27-4.18 (m, 2H), 3.85 (s, 3H), 3.44-3.30 (m, 2H), 2.13-2.00 (m, 2H), 1.43 (s, 9H). $^{13}$C NMR (100 MHz, CDCl$_3$): δ 170.1, 167.2, 158.4, 144.7, 142.3, 128.4, 126.1, 124.7, 119.1, 103.7, 79.5, 60.4, 52.5, 41.4, 37.7, 29.3, 28.4. MS: calculated for [C$_{21}$H$_{28}$N$_3$O$_6$]$^+$, 418.5 [M+H]$^+$; found 418.3.

tert-Butyl(S)-(3-((4-((2-(2-cyanopyrrolidin-1-yl)-2-oxoethyl)carbamoyl)quinolin-6-yl)oxy)propyl)carbamate (7): Compound 5 110 mg (0.21 mmol) and LiOH 30 mg (1.2 mmol) was stirred in 4 mL of H$_2$O/THF (1/1) for 6 hours. After most of the THF was removed under vacuum, the mixture was loaded onto a 25 g C18 cartridge (Silicycle, Canada) and eluded with a MeCN/water/TFA gradient (0/100/0.1 to 90/10/0.1) to remove the salts. The product 6 obtained was mixed with (S)-pyrrolidine-2-carbonitrile 53 mg (0.4 mmol), HOBT 68 mg (0.4 mmol), HBTU 152 mg (0.4 mmol) and DIPEA 0.56 mL (1.6 mmol) in dry 10 mL DMF. After 6 hours, the solvent was removed under vacuum and the remaining mixture was loaded onto a 25 g C18 cartridge (Silicycle, Canada). The product was purified with a MeCN/water/TFA gradient (0/100/0.1 to 90/10/0.1). 99 mg of 7 was obtained with a yield of 80%. 1H NMR (400 MHZ, CDCl$_3$): δ 8.73 (s, 1H), 7.95 (d, J=10.2 Hz, 1H), 7.68 (br s, 1H), 7.63-7.56 (m, 1H), 7.56-7.48 (m, 1H), 7.38-7.29 (m, 1H), 5.27 (br s, 1H), 4.84-4.72 (m, 1H), 4.46-4.35 (m, 1H), 4.33-4.20 (m, 1H), 4.17-4.09 (m, 2H), 3.78-3.64 (m, 1H), 3.59-3.46 (m, 1H), 3.36 (s, 2H), 2.38-2.17 (m, 4H), 1.42 (s, 9H), 1.35-1.27 (m, 2H). $^{13}$C NMR (100 MHZ, CDCl$_3$): δ 167.6, 167.5, 157.9, 156.2, 146.3, 130.2, 125.7, 123.7, 119.3, 118.0, 103.3, 79.0, 65.9, 46.8, 45.7, 42.2, 37.6, 29.8, 29.3, 28.4, 25.1. MS: calculated for [C$_{25}$H$_{32}$N$_5$O$_5$]+, 482.6 [M+H]$^+$; found 482.3.

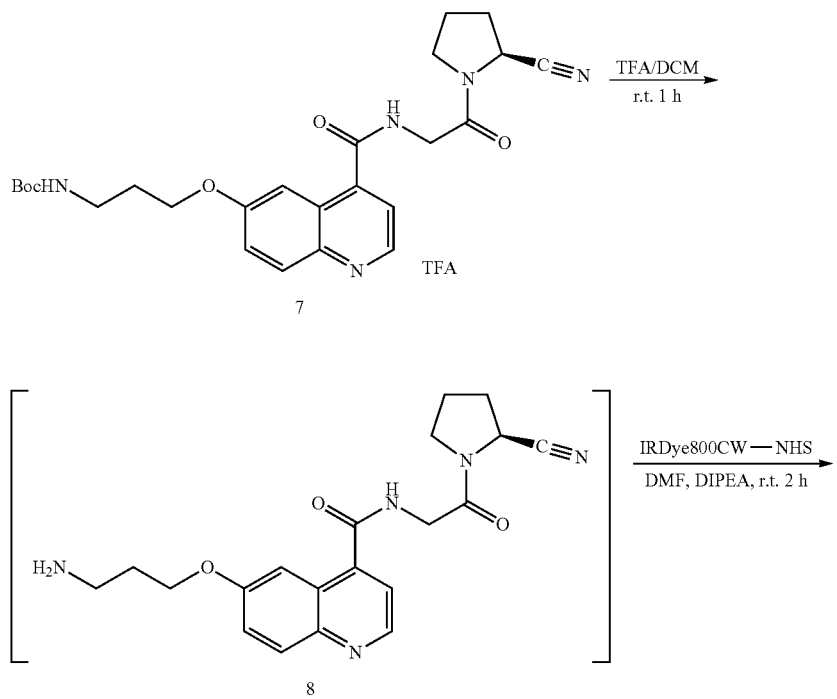

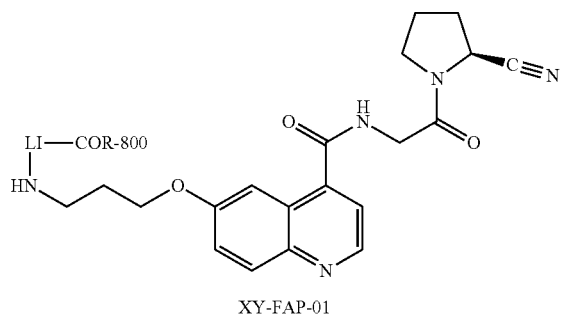

XY-FAP-01. Compound 7 (1 mg, 1.7 μmol) was treated with a 1 mL solution of TFA/methylene chloride (1/1) for 2 h. The solvent was removed under vacuum, and the remaining material re-dissolved in 0.5 mL of DMSO. To the solution, LICOR800CW-NHS ester 0.5 mg (0.43 μmol) and Et$_3$N 10 μL were added. After 1 h at room temperature, the solvent was removed and the product was purified by HPLC. 0.5 mg product was obtained with a yield of 85%. HPLC condition: column Phenomenex, Luna 10×250 mm, 10 u. Gradient 10/90/0.1 MeCN/H$_2$O/TFA to 80/20/0.1 MeCN/H$_2$O/TFA within 15 min at a flow of 3 mL/min. The product was eluted at 10.1 min. MS: Calculated for $[C_{66}H_{76}N_7O_{17}S_4]^+$, 1366.4[M+H]$^+$; found 1366.8.

1.2 Synthesis of XY-FAP-02

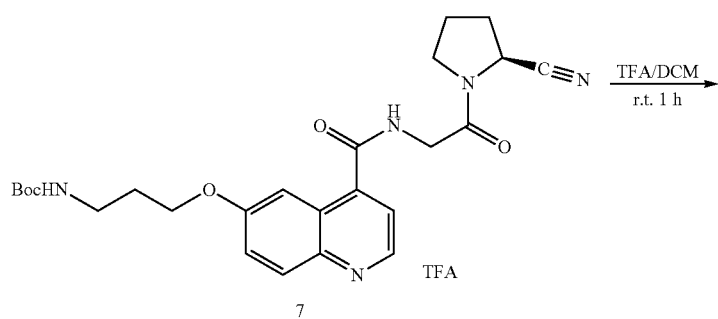

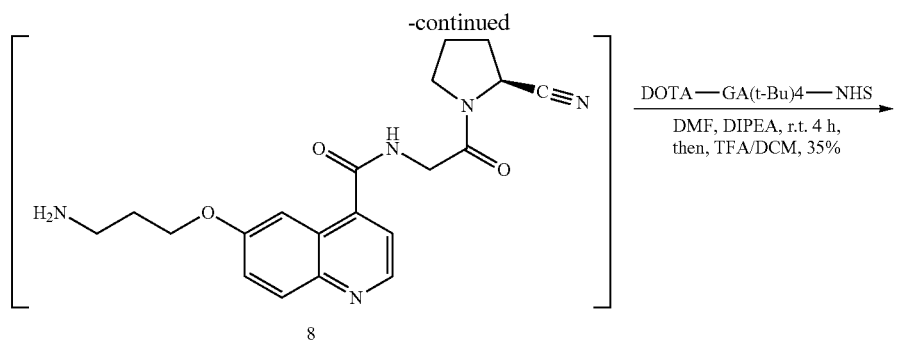

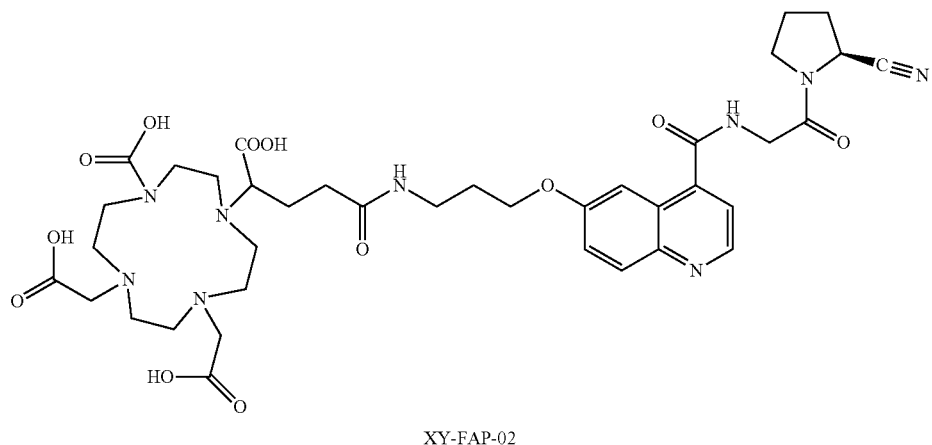

XY-FAP-02

2,2',2''-(10-(1-Carboxy-4-((3-((4-((2-((S)-2-cyanopyrrolidin-1-yl)-2-oxoethyl)carbamoyl)quinolin-6-yl)oxy)propyl)amino)-4-oxobutyl)-1,4,7,10-tetraazacyclododecane-1,4,7-triyl)triacetic acid (XY-FAP-02): Compound 7 (15 mg, 31.3 µmol) was treated with a 1-mL solution of TFA/methylene chloride (1/1) for 1 h. The solvent was removed under vacuum, and the remaining material re-dissolved in 0.5 mL of DMF. To the solution, DIPEA (27 µL, 156.5 µmol) was added, followed by dropwise addition of a solution of DOTA-GA(t-Bu)$_4$-NHS (25 mg, 31.3 µL) in 0.5 mL of DMF. The reaction mixture was stirred for 4 h at ambient temperature and then concentrated under vacuum. The t-Bu-protected intermediate was deprotected in situ without further purification using a 1 mL mixture of TFA, H$_2$O and triethylsilane (TES) (95:2.5:2.5). Reaction mixture was then concentrated and purified by semipreparative HPLC, to afford the product as a white solid (8.5 mg, 33% yield). MS: calculated for [C$_{39}$H$_{54}$N$_9$O$_{12}$]+, 840.9 [M+H]$^+$; found 840.5. HPLC (10 mm×250 mm Phenomenex Luna C18 column, 10 µm, mobile phase 95/5/0.1% to 75/25/0.1% water/acetonitrile/TFA over 20 min, flow 5 mL/min) XY-FAP-02 eluted at 11.8 min.

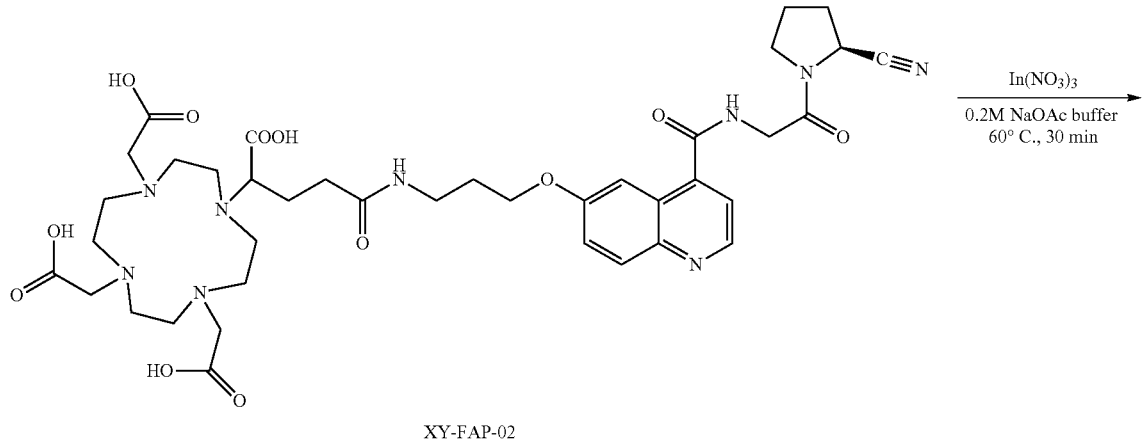

XY-FAP-02

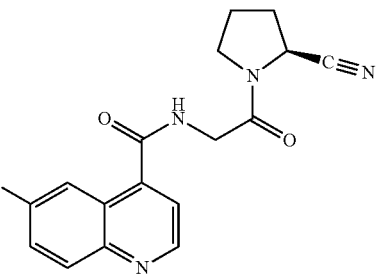
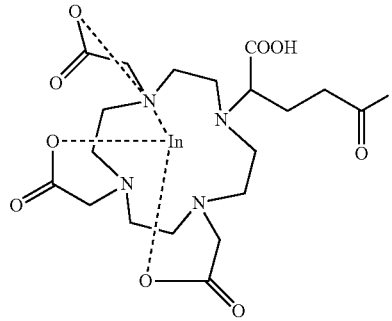

XY-FAP-02-[n]

XY-FAP-02-[In]. $^{113/115}$Indium(III) 2,2',2''-(10-(1-Carboxy-4-((3-((4-((2-((S)-2-cyanopyrrolidin-1-yl)-2-oxoethyl)carbamoyl)quinolin-6-yl)oxy)propyl)amino)-4-oxobutyl)-1,4,7,10-tetraazacyclododecane-1,4,7-triyl) triacetate (XY-FAP-02-[In]): To a solution of 2 mg (2.4 µmol) of XY-FAP-02 in 1 mL of 0.2M AcONa, a solution of 1.4 mg (4.6 µmol) of In(NO$_3$)$_3$ in 0.5 mL water is added and warmed in a 60° C. bath for 30 min. After cooling to ambient temperature, the mixture was purified by semipreparative HPLC. The product was obtained as a white solid (1.8 mg, 79% yield). MS: calculated for [C$_{39}$H$_{51}$N$_9$O$_{12}$In]$^+$, 951.7 [M+H]$^+$; found 952.5. HPLC (10 mm×250 mm Phenomenex Luna C18 column, 10 µm, mobile phase 95/5/0.1% to 75/25/0.1% water/acetonitrile/TFA over 20 min, flow 5 mL/min) XY-FAP-02-[In] eluted at 14.0 min.

1.3 Radiolabeling Methods. Briefly, 20 mg XY-FAP-02 solution in 20 mL of 0.2 M NaOAc was added to 10 mL 4.6 mCi $^{111}$InCl$_3$ solution (Nordion, Ottawa, Canada) and adjusted to a final pH of 5.5-6. The mixture was heated in a water bath at 70° C. for 30 min and, after the reaction completed, was diluted with 200 ml of water for HPLC purification. The solution was purified using a Phenomenex 5 µm C$_{18}$ Luna 4.6×250 mm2 column (Torrance, CA) with a flow rate of 0.6 mL/min with water (0.1% TFA) (A) and MeCN (0.1% TFA) (B) as the eluting solvents. An isocractic solution of 88% A and 12% B was utilized for purification, resulting in the labeled compound, $^{111}$In-XY-FAP-02, eluting first at 18.6 min followed by the unlabeled starting material at 23.5 min. 3.2 mCi of labeled compound was obtained as pure product with a yield of 69%. Another reaction with the identical condition was performed with 74% yield. The collected radioactivity was diluted with 20 mL of water and loaded onto activated Sep-Pak (WAT020515, Waters, Milford, MA). After the Sep-Pak was washed with 10 ml of water, $^{111}$In-XY-FAP-02 was eluted with 1.5 mL of ethanol. The ethanol was evaporated under a gentle stream of N$_2$ (to a total volume of <50 µL). The resulting solution was formulated in saline for the imaging and biodistribution studies.

1.4 FAP Inhibition Assay. The inhibitory activity of XY-FAP-01 was determined using a fluorogenic FAP Assay Kit (BPS Bioscience, San Diego, CA). Briefly, XY-FAP-01, DPP substrate, and human recombinant FAP were loaded into a 96 well plate to initiate the enzyme reaction. The reaction was left for 10 minutes at room temperature before fluorescence was measured with a VICTOR3 V multilabel plate reader (PerkinElmer Inc., Waltham, MA). Data was normalized and semi-log inhibition curves were generated in order to determine the IC50 value (concentration of XY-FAP-01 where the enzyme activity is 50% inhibited) for XY-FAP-01 and subsequent enzyme inhibition constant (Ki) using the Cheng-Prusoff conversion. Generation of semi-log inhibition curves and IC50 values were done using GraphPad Prism (San Diego, CA).

1.5 Cell lines. Six human cancer cell lines were used to assess binding to FAP: glioblastoma (U-87-MG), melanoma (SK-MEL-24), prostate (PC-3), non-small cell lung cancer (NCI-H2228), colorectal carcinoma (HCT 116), and lung squamous cell carcinoma (NCI-H226). From the literature, U-87-MG, SK-MEL-24, and NCI-H$_{2228}$ cell lines were identified as having high levels of FAP expression [FAP-positive (+)] whereas PC-3, NCI-H226, and HCT 116 cells expressed very low levels of FAP [FAP-negative(−)]. These expression profiles were further confirmed via flow cytometry with an APC-conjugated anti-FAP antibody (R&D Systems, Minneapolis, MN) and quantitative real-time PCR. All cell lines were purchased from American Type Culture Collection (ATCC, Manassas, VA).

U-87-MG cells were maintained in MEM medium (Corning Cellgro, Manassas, VA), containing 10% fetal bovine serum (FBS) (Sigma-Aldrich, St. Louis, MO) and 1% penicillin-streptomycin (Corning Cellgro, Manassas, VA), supplemented with sodium bicarbonate (Corning), sodium pyruvate (Gibco, Gaithersburg, MD), and MEM non-essential amino acids (Gibco). SK-MEL-24 cells were maintained in MEM medium, containing 15% FBS and 1% penicillin-streptomycin, supplemented with sodium bicarbonate, sodium pyruvate, and MEM non-essential amino acids. PC-3 cells were grown in Ham's F-12K medium (Corning Cellgro) supplemented with 10% FBS and 1% penicillin-streptomycin. NCI-H2228, NCI-H$_{226}$, and HCT 116 cells were cultured in RPMI 1640 medium (Corning Cellgro) supplemented with 10% FBS and 1% penicillin-streptomycin. All cell cultures were maintained at 37° C. and 5% carbon dioxide (CO$_2$) in a humidified incubator.

1.6 Cellular Uptake Studies. All cellular uptake and specific binding studies were performed in triplicate to ensure reproducibility. Cells were detached using 0.05% trypsin (Corning), resuspended in 1 million cell aliquots in binding buffer, and incubated with various concentrations (range, 50 nM to 0.78 nM) of XY-FAP-01 for 1 hour at 37° C. and 5% CO$_2$. To assess the specific uptake of XY-FAP-02, cells were preblocked with a FAP and DPP-IV specific inhibitor (Val-boroPro, MilliporeSigma, Burlington, MA) or a DPP-IV specific inhibitor (Sitagliptin, Santa Cruz Biotechnology, Inc., Dallas, TX) at various concentrations (range, 10-10 M to 104 M) prior to incubation with 25 nM XY-FAP-02 solution in binding buffer for 1 hour at 37° C. and 5% $CO_2$. Cellular uptake was terminated by washing cells with ice cold PBS (1×) three times. Cells were resuspended in binding buffer and transferred to a 96-well plate for imaging. Images were acquired on the LI-COR Pearl Impulse Imager (Lincoln, NE) using an excitation wavelength of 785 nm and detection of the emission wavelength at 800 nm. Images were analyzed using the LI-COR Pearl Impulse Software (Version 2.0) and fluorescence intensity was corrected for background signal and normalized to well area.

Cellular Uptake of $^{111}$In-XY-FAP-02 was also assessed in cells. Cell aliquots (1 million) were incubated with 1 µCi $^{111}$In-XY-FAP-02 in saline for 30 minutes at 37° C. and 5% $CO_2$. Cells were washed three times with cold PBS (1×) and activity of the cell pellets was measured with the 1282 CompuGamma CS gamma well counter (Pharmacia/LKB Nuclear, Inc., Gaithersburg, MD). The percent uptake of the administered activity was calculated by comparison with samples of a standard dose.

1.7 Small-Animal Near Infrared Fluorescence (NIRF) Imaging. NIRF images were acquired on the LI-COR Pearl Impulse Imager using an excitation wavelength of 785 nm and a detection wavelength of 800 nm. Mice utilized for imaging studies were anesthetized with 3% isofluorane (v/v) and maintained at 1.5% isofluorane for the imaging procedure. NOD/SKID mice bearing FAP+ U-87-MG and FAP-PC-3 tumor xenografts were injected with 10 nmol of XY-FAP-01 via tail vein injection and images were acquired at 30 min, 1 h, 2 h, 2.5 h, and 4 h after injection of tracer. Data were displayed and analyzed using the LI-COR Pearl Impulse Software (Version 2.0).

1.8 Small-Animal SPECT-CT Imaging. SPECT-CT studies were performed on NOD/SKID mice bearing FAP+U-87-MG and FAP-PC-3 tumor xenografts. For imaging studies, mice were anesthetized with 3% isoflurane prior to being placed on the scanner bed and kept warm with an external light source. Isoflurane levels were decreased to 1.5% for the rest of the imaging procedure. After mice were injected with 300 µCi $^{111}$In-XY-FAP-02 in 200 µL saline, SPECT-CT imaging was carried out using a CT-equipped Gamma Medica-Ideas SPECT scanner (Northridge, CA) at the indicated timepoints (30 min, 2 h, 6 h, and 24 h) post radiotracer injection. A CT scan was performed at the end of each SPECT scan for anatomical co-registration. Obtained data sets were reconstructed using the provided Gamma Medica-Ideas software and final data visualization and image generation were prepared using Amira® software (FEI, Hillsboro, OR).

1.9 Ex-vivo Biodistribution. NOD/SKID mice bearing FAP+U-87-MG and FAP-PC-3 tumor xenografts were injected with 10 µCi $^{111}$In-XY-FAP-02 in 200 µL saline via the tail vein. At 5 min, 30 min, 2 h, 6 h, and 12 hr post injection, mice (n=4) were sacrificed by $CO_2$ asphyxiation and blood was immediately collected by cardiac puncture. Additionally, the heart, lungs, liver, stomach, pancreas, spleen, fat, kidney, small intestine, large intestine, bladder, muscle, femur, FAP+U-87-MG xenograft, and FAP-PC-3 xenograft were collected for biodistribution analysis. Each tissue was weighed and radioactivity was measuring using a 2480 Wizard$^2$ automated gamma counter (PerkinElmer, Waltham, MA). Radioactivity measurements were corrected for decay and compared with samples of a standard dilution of the initial dose to calculated percent injected dose per gram (% ID/g).

For blocking studies, mice (n=5 per group) were co-injected with unlabeled XY-FAP-02 (50 µg per mouse) and 10 µCi $^{111}$In-XY-FAP-02 in 200 µL saline. Mice (n=5) injected with 10 µCi $^{111}$In-XY-FAP-02 in 200 µL saline served as a control. At 6 h post injection, mice were sacrificed, tissues were collected, and radioactivity was measured with the gamma well counter.

1.10 Data Analysis. Data are expressed at mean±standard deviation (SD). Prism software (GraphPAD, San Diego, CA) was used for analysis and statistical significance was calculated using a two-tailed Student's t test. A P-value <0.05 was considered significant.

1.11 Xenograft Tumor Model. 6-week old female NOD/SCID mice were subcutaneously injected in the upper left and right flanks with 1 million U87(FAP+) cells and PC3 cells (FAP-) in RPMI 1640 media supplemented with 1% FBS. Mice were monitored for tumor size and used for optical or SPECT/CT imaging when the size of tumor reached around 100 mm3.

Example 2

Representative Results 2.1 FAP Inhibitory Assay. XY-FAP-01 demonstrated high binding affinity to human recombinant FAP. The enzyme inhibitory constant (Ki) for the compound was determined to be 1.26 nM.

2.2 Cellular Uptake Studies. FAP-positive cell lines showed concentration dependent uptake of XY-FAP-01 whereas FAP-negative cell lines showed no significant binding of XY-FAP-01 at all concentrations (see, e.g., FIG. 3A). Saturated binding of XY-FAP-01 was observed at concentration of 25 nM, which was subsequently used as the base concentration for all binding inhibition studies. When preblocked with a FAP and DPP-IV specific inhibitor, XY-FAP-01 binding was significantly inhibited in FAP-positive cells (FIG. 3B). Interestingly, this phenomenon was not observed in FAP-positive cell lines preblocked with a DPP-IV specific inhibitor. These results further justify the specificity of XY-FAP-01 for FAP over DPPIV, since blocking of DPPIV did not result in a change of binding ability of XY-FAP-01.

Similar specificity was observed with the radioactive analog, 111 In-XY-FAP-02. FAP positive cell line, U-87-MG, demonstrated over 30% uptake of administered radioactive dose after incubation whereas the FAP negative cell line, PC-3, had uptake of 0.01% of administered dose (FIG. 3C). Taken together, these results support the specificity of XY-FAP-01 and 111 In-XY-FAP-02 in the engagement of FAP in vitro.

2.3 Ex-vivo Biodistribution. Ex-vivo biodistribution of 111 In-XY-FAP-02 results correlated with the observed imaging results (FIG. 4). Initially, the blood pool activity is very high, with over 10% % ID/g at 30 minutes post injection. With clearance of the compound, we see the blood pool activity drop significantly after 2 hours of distribution and remained less than 5% % ID/g from 2 hours post injection (FIG. 5A). High activity was also observed in pancreas, small intestines, and bladder until 2 hours post injection. Positive tumor uptake peaked at 30 minutes post injection and remained between 13-11% % ID/g up to 6 hours. Washout of tumor was observed at 12 hours post injection, with % ID/g dropping to below 5%. The PC-3, FAP negative xenograft had less than 3.5% % ID/g for all timepoints.

Co-injection of cold compound with 111 In-XY-FAP-02 resulted in significant blocking of tracer uptake in U-87 xenografts, with % ID/g dropping from 11.20% without blocking versus 0.27% with blocking (p<0.0001). Additionally, blocking with cold compound resulted in % ID/g of all tissues dropping significantly, with most values being less than 0.1%. This decrease in uptake is most likely due to the blocking of non-specific binding of tracer to non-target tissues and the blocking of specific binding of FAP in U-87 xenografts.

2.4 Small-Animal Near Infrared Fluorescence (NIRF) Imaging. NIRF imaging of XY-FAP-01 demonstrated specific uptake of tracer in the U-87-MG xenograft as early as 30 minutes post injection (FIG. 6). After one hour of distribution, tracer clearance via the bladder was observed with retained tracer uptake in the FAP positive xenograft. Tracer uptake was retained in the positive xenograft after four hours of distribution. In contrast, no significant uptake of tracer was observed in the FAP negative tumor at all imaging time points.

REFERENCES

All publications, patent applications, patents, and other references mentioned in the specification are indicative of the level of those skilled in the art to which the presently disclosed subject matter pertains. All publications, patent applications, patents, and other references (e.g., websites, databases, etc.) mentioned in the specification are herein incorporated by reference in their entirety to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

Allinen M, Beroukhim R, Cai L, Brennan C, Lahti-Domenici J, Huang H, Porter D, Hu M, Chin L, Richardson A, Schnitt S, Sellers W R, Polyak K. Molecular characterization of the tumor microenvironment in breast cancer. Cancer Cell. 2004 July; 6(1):17-32.

Bae S, Park C W, Son H K, Ju H K, Paik D, Jeon C J, Koh G Y, Kim J, Kim H. Fibroblast activation protein alpha identifies mesenchymal stromal cells from human bone marrow. Br J Haematol. 2008 September; 142(5):827-30.

Chen Z Y, Wang Y X, Lin Y, Zhang J S, Yang F, Zhou Q L, Liao Y Y. Advance of molecular imaging technology and targeted imaging agent in imaging and therapy. Biomed Res Int. 2014; 2014: 819324. PMCID: PMC3943245.

Coenen H H, Elsinga P H, Iwata R, Kilbourn M R, Pillai M R, Rajan M G, Wagner H N Jr. Zaknun J J. Fluorine-18 radiopharmaceuticals beyond [18F]FDG for use in oncology and neurosciences. Nuclear medicine and biology. 2010; 37:727-740.

Coenen H H, Elsinga P H, Iwata R, Kilbourn M R, Pillai M R, Rajan M G, Wagner H N Jr. Zaknun J J. Fluorine-18 radiopharmaceuticals beyond [18F]FDG for use in oncology and neurosciences. Nuclear medicine and biology. 2010; 37:727-740. Biodistribution, tumor detection, and radiation dosimetry of 18F-DCFBC, a low-molecular-weight inhibitor of prostate-specific membrane antigen, in patients with metastatic prostate cancer. Journal of nuclear medicine: official publication, Society of Nuclear Medicine. 2012; 53:1883-1891.

Edosada C Y, Quan C, Tran T, Pham V, Wiesmann C, Fairbrother W, Wolf B B. Peptide substrate profiling defines fibroblast activation protein as an endopeptidase of strict Gly(2)-Pro(1)-cleaving specificity. FEBS Lett. 2006 Mar. 6; 580(6):1581-6.

Fischer E, Chaitanya K, Wuest T, et al. Radioimmunotherapy of fibroblast activation protein positive tumors by rapidly internalizing antibodies. Clin Cancer Res. 2012; 18:6208-6218.

Franco O E, Shaw A K, Strand D W, Hayward S W. Cancer associated fibroblasts in cancer pathogenesis. Semin Cell Dev Biol. 2010 February; 21(1):33-9.

Garin-Chesa P, Old L J, Rettig W J. Cell surface glycoprotein of reactive stromal fibroblasts as a potential antibody target in human epithelial cancers. Proc Natl Acad Sci USA. 1990 September; 87(18):7235-9. PMCID: PMC54718.

Jansen K, Heirbaut L, Cheng J D, Joossens J, Ryabtsova O, Cos P, Maes L, Lambeir A M, De Meester I, Augustyns K, Van der Veken P. Selective Inhibitors of Fibroblast Activation Protein (FAP) with a (4-Quinolinoyl)-glycyl-2-cyanopyrrolidine Scaffold. ACS Med Chem Lett. 2013 Mar. 18; 4(5):491-6.

Jansen K, Heirbaut L, Verkerk R, Cheng J D, Joossens J, Cos P, Maes L, Lambeir A M, De Meester I, Augustyns K, Van der Veken P. Extended structure-activity relationship and pharmacokinetic investigation of (4-quinolinoyl)glycyl-2-cyanopyrrolidine inhibitors of fibroblast activation protein (FAP). J Med Chem. 2014 Apr. 10; 57(7):3053-74.

Kelly T. Fibroblast activation protein-alpha and dipeptidyl peptidase IV (CD26): cell-surface proteases that activate cell signaling and are potential targets for cancer therapy. Drug Resist Updat. 2005 February-April; 8(1-2):51-8.

Kraman M, Bambrough P J, Arnold J N, Roberts E W, Magiera L, Jones J O, Gopinathan A, Tuveson D A, Fearon D T. Suppression of antitumor immunity by stromal cells expressing fibroblast activation protein-alpha. Science. 2010 Nov. 5; 330(6005):827-30.

Laverman P, van der Geest T, Terry S Y, Gerrits D, Walgreen B, Helsen M M, Nayak T K, Freimoser-Grundschober A, Waldhauer I, Hosse R J, Moessner E, Umana P, Klein C, Oyen W J, Koenders M I, Boerman O C. Immuno-PET and Immuno-SPECT of Rheumatoid Arthritis with Radiolabeled Anti-Fibroblast Activation Protein Antibody Correlates with Severity of Arthritis. J Nucl Med. 2015 May; 56(5):778-83.

Lo P C, Chen J, Stefflova K, Warren M S, Navab R, Bandarchi B, Mullins S, Tsao M, Cheng J D, Zheng G. Photodynamic molecular beacon triggered by fibroblast activation protein on cancer-associated fibroblasts for diagnosis and treatment of epithelial cancers. J Med Chem. 2009 Jan. 22; 52(2):358-68.

Poplawski S E, Lai J H, Li Y, Jin Z, Liu Y, Wu W, Wu Y, Zhou Y, Sudmeier J L, Sanford D G, Bachovchin W W. Identification of selective and potent inhibitors of fibroblast activation protein and prolyl oligopeptidase. J Med Chem. 2013 May 9; 56(9):3467-77.

Reilly R M, Lam K, Chan C, Levine M. Advancing Novel Molecular Imaging Agents from Preclinical Studies to First-in-Humans Phase I Clinical Trials in Academia-A Roadmap for Overcoming Perceived Barriers. Bioconjugate chemistry. 2015; 26:625-632.

Rettig W J, Garin-Chesa P, Healey J H, Su S L, Ozer H L, Schwab M, Albino A P, Old L J. Regulation and heteromeric structure of the fibroblast activation protein in normal and transformed cells of mesenchymal and neuroectodermal origin Cancer Res. 1993 Jul. 15; 53(14): 3327-35.

Ryabtsova O, Jansen K, Van Goethem S, Joossens J, Cheng J D, Lambeir A M, De Meester I, Augustyns K, Van der Veken P. Acylated Gly-(2-cyano)pyrrolidines as inhibitors of fibroblast activation protein (FAP) and the issue of FAP/prolyl oligopeptidase (PREP)-selectivity. Bioorg Med Chem Lett. 2012 May 15; 22(10):3412-7.

Scanlan M J, Raj B K, Calvo B, Garin-Chesa P, Sanz-Moncasi M P, Healey J H, Old L J, Rettig W J. Molecular cloning of fibroblast activation protein alpha, a member of the serine protease family selectively expressed in stromal fibroblasts of epithelial cancers. Proc Natl Acad Sci USA. 1994 Jun. 7; 91(12):5657-61.

Scott A M, Wiseman G, Welt S, Adjei A, Lee F T, Hopkins W, Divgi C R, Hanson L H, Mitchell P, Gansen D N, Larson S M, Ingle J N, Hoffman E W, Tanswell P, Ritter G, Cohen L S, Bette P, Arvay L, Amelsberg A, Vlock D, Rettig W J, Old L J. A Phase I dose-escalation study of sibrotuzumab in patients with advanced or metastatic fibroblast activation protein-positive cancer. Clin Cancer Res. 2003 May; 9(5): 1639-47.

Tsai T Y, Yeh T K, Chen X, Hsu T, Jao Y C, Huang C H, Song J S, Huang Y C, Chien C H, Chiu J H, Yen S C, Tang H K, Chao Y S, Jiaang W T. Substituted 4-carboxymethylpyroglutamic acid diamides as potent and selective inhibitors of fibroblast activation protein. J Med Chem. 2010 Sep. 23; 53(18):6572-83.

Tuxhorn J A, Ayala G E, Smith M J, Smith V C, Dang T D, Rowley D R. Reactive stroma in human prostate cancer: induction of myofibroblast phenotype and extracellular matrix remodeling. Clin Cancer Res. 2002 September; 8(9):2912-23.

Welt S, Divgi C R, Scott A M, Garin-Chesa P, Finn R D, Graham M, Carswell E A, Cohen A, Larson S M, Old L J, et al, Antibody targeting in metastatic colon cancer: a phase I study of monoclonal antibody F19 against a cell-surface protein of reactive tumor stromal fibroblasts. J Clin Oncol. 1994 June; 12(6):1193-203.

Youn H., Hong K. In vivo noninvasive small animal molecular imaging. Osong Public Health Res Perspect. 2012; 3:48-59. PMCID: PMC3738683.

Yu D M, Yao T W, Chowdhury S, Nadvi N A, Osborne B, Church W B, McCaughan G W, Gorrell M D. The dipeptidyl peptidase I V family in cancer and cell biology. FEBS J. 2010 March; 277(5):1126-44.

U.S. Patent Application Publication No. US2014/0357650 for Novel FAP Inhibitors to Jansen et al., published Dec. 4, 2014.

U.S. Pat. No. 9,346,814 for Novel FAP Inhibitors to Jansen et al., issued May 24, 2016.

International PCT Patent Publication No. WO 2013/107820 for Novel FAP Inhibitors to Jansen et al., published Jul. 25, 2013.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A low molecular weight compound of Formula (I):

B-L-A  (I)

wherein:

A is a targeting moiety for FAP-α, wherein A has the structure of:

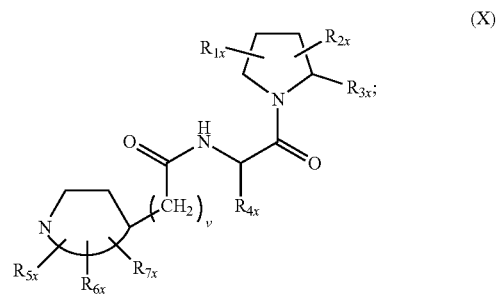

(X)

wherein:

$R_{1x}$ and $R_{2x}$ are each independently selected from the group consisting of H, OH, halogen, $C_{1-6}$alkyl, —O-$C_{1-6}$alkyl, and —S-$C_{1-6}$alkyl;

$R_{3x}$ is selected from the group consisting of H, —CN, —B(OH)$_2$ —C(O) alkyl, —C(O)aryl-, —C≡C—C(O) aryl, —C≡C—S(O)$_2$aryl, —CO$_2$H, —SO$_3$H, —SO$_2$NH$_2$, —PO$_3$H$_2$, and 5-tetrazolyl;

$R_{4x}$ is H;

$R_{5x}$, $R_{6x}$ and $R_{7x}$ are H;

v is 0; and

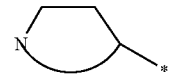

represents a quinolinyl ring having a point of attachment to a remainder of the FAP binding moiety at the 4-position of the quinolinyl ring;

B is any optical or radiolabeled functional group suitable for optical imaging, positron-emission tomography (PET) imaging, single-photon emission computed tomography (SPECT) imaging, or radiotherapy; and L is a linker having bi-functionalization adapted to form a chemical bond with B and A; or a stereoisomer, tautomer, racemate, salt, hydrate, or solvate thereof.

2. The compound of claim 1, wherein $R_{1x}$ and $R_{2x}$ are each independently selected from the group consisting of H and F.

3. The compound of claim 2, wherein $R_{3x}$ is —CN.

4. The compound of claim 3, wherein B comprises a chelating agent.

* * * * *

UNITED STATES PATENT AND TRADEMARK OFFICE
CERTIFICATE OF CORRECTION

| | | |
|---|---|---|
| PATENT NO. | : 12,115,233 B2 | Page 1 of 1 |
| APPLICATION NO. | : 18/585905 | |
| DATED | : October 15, 2024 | |
| INVENTOR(S) | : Xing Yang et al. | |

It is certified that error appears in the above-identified patent and that said Letters Patent is hereby corrected as shown below:

In the Claims

Column 64, Claim 1, Line 32-33 reads:
- -B (OH)$_2$ -C(O) alkyl, -C(O)aryl-, -C-C-C(O) aryl, -C-C-S(O)$_2$aryl, - CO$_2$H, -SO$_3$H, -

Whereas it should read:
- -B (OH)$_2$ -C(O) alkyl, -C(O)aryl-, -C=C-C(O) aryl, -C=C-S(O)$_2$aryl, - CO$_2$H, -SO$_3$H, -

Signed and Sealed this
Thirty-first Day of December, 2024

Derrick Brent
*Acting Director of the United States Patent and Trademark Office*